(12) United States Patent
Ross et al.

(10) Patent No.: US 7,446,183 B2
(45) Date of Patent: Nov. 4, 2008

(54) FUSION PROTEIN COMPRISING GROWTH HORMONE AND GROWTH HORMONE RECEPTOR

(75) Inventors: Richard Ross, Sheffield (GB); Peter Artymiuk, Sheffield (GB); Jon Sayers, Sheffield (GB)

(73) Assignee: Asterion Limited, Sheffield (GB)

( * ) Notice: Subject to any disclaimer, the term of this patent is extended or adjusted under 35 U.S.C. 154(b) by 0 days.

(21) Appl. No.: 10/311,473

(22) PCT Filed: Jun. 18, 2001

(86) PCT No.: PCT/GB01/02645

§ 371 (c)(1),
(2), (4) Date: Jul. 18, 2003

(87) PCT Pub. No.: WO01/96565

PCT Pub. Date: Dec. 20, 2001

(65) Prior Publication Data

US 2004/0071655 A1 Apr. 15, 2004

(30) Foreign Application Priority Data

| Jun. 16, 2000 | (GB) | ................................. 0014765.2 |
| Mar. 10, 2001 | (GB) | ................................. 0105969.0 |
| Mar. 16, 2001 | (GB) | ................................. 0106487.2 |

(51) Int. Cl.
| C07K 14/61 | (2006.01) |
| C07K 1/10 | (2006.01) |
| C07H 19/00 | (2006.01) |
| C07H 21/04 | (2006.01) |
| C12N 15/63 | (2006.01) |
| C12N 1/19 | (2006.01) |
| C12N 5/10 | (2006.01) |
| C12N 1/21 | (2006.01) |
| A61K 38/27 | (2006.01) |
| C12P 21/02 | (2006.01) |

(52) U.S. Cl. .................... 530/399; 536/23.4; 435/320.1; 435/254.2; 435/325; 435/348; 435/419; 435/366; 435/252.3; 435/69.7; 514/12; 530/815

(58) Field of Classification Search .................... 514/12; 530/350; 424/85.2
See application file for complete search history.

(56) References Cited

U.S. PATENT DOCUMENTS 4,857,637 A    8/1989   Martin et al.

FOREIGN PATENT DOCUMENTS

| EP | 0 741 187   | 11/1996 |
| EP | 0 950 710   | 10/1999 |
| WO | WO 86/05804 | 10/1986 |
| WO | WO 90/05185 | 5/1990  |

(Continued)

OTHER PUBLICATIONS

Baumann et al, 1989, Metabolism. 38(4): 330-333.*

(Continued)

*Primary Examiner*—Elizabeth C. Kemmerer
*Assistant Examiner*—Zachary C Howard
(74) *Attorney, Agent, or Firm*—Crowell & Moring LLP

(57) ABSTRACT

This invention relates to agents which bind to cell surface receptors; methods to manufacture said agents; therapeutic compositions comprising said agents; and screening methods to identify novel agents.

35 Claims, 28 Drawing Sheets

FOREIGN PATENT DOCUMENTS

| WO | WO 92/21029 | | 11/1992 |
|---|---|---|---|
| WO | WO 97/32891 | | 9/1997 |
| WO | WO 99/02552 | | 1/1999 |
| WO | WO 9902552 | A2 * | 1/1999 |
| WO | WO 9902710 | A1 * | 1/1999 |
| WO | WO 00 18932 | | 4/2000 |

OTHER PUBLICATIONS

Fernandez-Botran et al 2002. Expert Opin Biol Ther. 2(6): 585-605.*
Renne et al, 1998. Journal of Biological Chemistry. 273(42): 27213-27219.*
Takahashi et al 1997. J Clin Invest. 100(5): 1159-1165.*
Desplancq et al 1994. Protein Engineering, 7(8): 1027-1033.*
Baumann. 2001. J Pediatr Endocrinol Metab. 14(4): 355-375.*
Kopchick et al 2000, Molecular Genetics and Metabolism, 71: 293-314.*
Tchelet, 1997. Molecular and Cellular Endocrinology. 130: 141-152.*
Phillips, A., J Pharm Pharmacology 53: 1169-1174, 2001.*
Wilkinson et al, Sep. 2007. Nature Medicine. 13(9): 1108-1113.*
R. Ross et al., "A short isoform of the human growth hormone receptor functions as a dominant negative inhibitor of the full-length receptor and generates large amounts of binding protein" Molecular Endocrinology, vol. 11, No. 3 (1997) pp. 265-173 XP002181691.
P. Moran et al., "A nonfunctional sequence converted to a signal for glycophosphatidylinositol membrane anchor attachment". Journal of Cell Biology, vol. 115, No. 2 (1991) pp. 329-336, XP001031102.
Zhang Yiying et al. "Positional cloning of the mouse obese gene and its human homolouge". Nature, MacMillan Journals Ltd. London, vol. 372, No. 6505, Dec. 1, 1994, pp. 425-432, XP000602062.
L. Tartaglia et al. "Identification and expression cloning of a leptin receptor, OB-R", Cell, Cell Press, vol. 83, No. 7, Dec. 29, 1995, pp. 1263-1271, XP000602068.
M. Hibi et al. "Molecular Cloning and Expression of an IL-6 Signal Transducer GP130", Cell, Cell Press, Cambridge, vol. 63, Dec. 21, 1990, pp. 1149-1157, XP002931740.

* cited by examiner

Figure 2:

ttcccaaccattcccttatccaggcttttttgacaacgctatgctccgcgcccatcgtctgcaccagctggcctttgacacctaccag
gagtttgaagaagcctatatcccaaaggaacagaagtattcattcctgcagaaccccccagacctccctctgtttctcagagtctat
tccgacaccctccaacagggaggaaacacaacagaaatccaacctagagctgctccgcatctccctgctgctcatccagtcgt
ggctggagcccgtgcagttcctcaggagtgtcttcgccaacagcctggtgtacggcgcctctgacagcaacgtctatgacctc
ctaaaggacctagaggaaggcatccaaacgctgatggggaggctggaagatggcagcccccggactgggcagatcttcaa
gcagacctacagcaagttcgacacaaactcacacaacgatgacgcactactcaagaactacgggctgctctactgcttcagga
aggacatggacaaggtcgagacattcctgcgcatcgtgcagtgccgctctgtggagggcagctgtggcttcggcggccgc*tg*
*ataa*

Figure 3:

gggaaagaattcgaaatagtgcaaccagatccacccattgccctcaactggactttactgaacgtcagtttaactgggattcatg
cagatatccaagtgagatgggaagcaccacgcaatgcagatattcagaaaggatggatggttctggagtatgaacttcaataca
aagaagtaaatgaaactaaatggaaaatgatggaccctatattgacaacatcagttccagtgtactcattgaaagtggataagga
atatgaagtgcgtgtgagatccaaacaacgaaactctggaaattatggcgagttcagtgaggtgctctatgtaacacttcctcag
atgagccaatttacatgtgaagaagatttctac*tgataa*aagcttgggaaa

Figure 4

GHstop ttcccaaccattcccttatccaggcttttgacaacgctatgctccgcgcccatcgtctgcaccagctggcctttgacacctaccag
gagtttgaagaagcctatatcccaaaggaacagaagtattcattcctgcagaaccccagacctccctctgtttctcagagtctat
tccgacaccctccaacagggaggaaacacaacagaaatccaacctagagctgctccgcatctccctgctgctcatccagtcgt
ggctggagcccgtgcagttcctcaggagtgtcttcgccaacagcctggtgtacggcgcctctgacagcaacgtctatgacctc
ctaaaggacctagaggaaggcatccaaacgctgatggggaggctggaagatggcagccccggactgggcagatcttcaa
gcagacctacagcaagttcgacacaaactcacacaacgatgacgcactactcaagaactacgggctgctctactgcttcagga
aggacatggacaaggtcgagacattcctgcgcatcgtgcagtgccgctctgtggagggcagctgtggcttcggcggccgc*tg
ataa*

GHR aagggcgaattcgaaatagtgcaaccagatccacccattgccctcaactggactttactgaacgtcagtttaactgggattcatg
cagatatccaagtgagatgggaagcaccacgcaatgcagatattcagaaaggatggatggttctggagtatgaacttcaataca
aagaagtaaatgaaactaaatggaaaatgatggaccctatattgacaacatcagttccagtgtactcattgaaagtggataagga
atatgaagtgcgtgtgagatccaaacaacgaaactctggaaattatggcgagttcagtgaggtgctctatgtaacacttcctcag
atgagccaatttacatgtgaagaagatttctac*tgataa*aagctt

Figure 5:

Growth Hormone:
ttcccaaccattcccttatccaggcttttgacaacgctatgctccgcgcccatcgtctgcaccagctggcctttgacacctaccag
gagtttgaagaagcctatatcccaaaggaacagaagtattcattcctgcagaaccccagacctccctctgtttctcagagtctat
tccgacaccctccaacagggaggaaacacaacagaaatccaacctagagctgctccgcatctccctgctgctcatccagtcgt
ggctggagcccgtgcagttcctcaggagtgtcttcgccaacagcctggtgtacggcgcctctgacagcaacgtctatgacctc
ctaaaggacctagaggaaggcatccaaacgctgatggggaggctggaagatggcagcccccggactgggcagatcttcaa
gcagacctacagcaagttcgacacaaactcacacaacgatgacgcactactcaagaactacgggctgctctactgcttcagga
aggacatggacaaggtcgagacattcctgcgcatcgtgcagtgccgctctgtggagggcagctgtggcttcggcggccgc

Linker
<u>ggtggcggaggtagtggtggcggaggtagcggtggcggaggttctggtggcggaggttcc</u>

Growth hormone receptor
gaattcgaaatagtgcaaccagatccacccattgccctcaactggactttactgaacgtcagtttaactgggattcatgcagatat
ccaagtgagatgggaagcaccacgcaatgcagatattcagaaaggatggatggttctggagtatgaacttcaatacaaagaag
taaatgaaactaaatggaaaatgatggaccctatattgacaacatcagttccagtgtactcattgaaagtggataaggaatatgaa
gtgcgtgtgagatccaaacaacgaaactctggaaattatggcgagttcagtgaggtgctctatgtaacacttcctcagatgagcc
aatttacatgtgaagaagatttctac*tgataa*aagctt

Figure 6

FptiplsrlfdnamlrahrlhqlafdtyqefeeayipkeqkysflqnpqtslcfsesiptpsnreetqqksnlellrislIliqswlepvqflrs
vfanslvygasdsnvydllkdleegiqtlmgrledgsprtgqifkqtyskfdtnshnddallknygllycfrkdmdkvetflrivqcrsve
gscgfggrggggsggggsggggsggggsefeivqpdppialnwtllnvsltgihadiqvrweaprnadiqkgwmvleyelqykevn
etkwkmmdpilttsvpvyslkvdkeyevrvrskqrnsgnygefsevlyvtlpqmsqftceedfy**kl

Figure 7 gggaaagaattcttttctggaagtgaggccacagcagctatccttagcagagcaccctggagtctgcaaagtgttaatccagg cctaaagacaaattcttctaaggagcctaaattcaccaagtgccgttcacctgagcgagagacttttcatgccactggacagat gaggttcatcatggtacaaagaacctaggacccatacagctgttctataccagaaggaacactcaagaatggactcaagaatg gaaagaatgccctgattatgtttctgctggggaaaacagctgttactttaattcatcgtttacctccatctggatiaccttattgtatcaa gctaactagcaatggtggtacagtggatgaaaagtgtttctctgttgatgaaatagtgcaaccagatccacccattgccctcaact ggactttactgaacgtcagtttaactgggattcatgcagatatccaagtgagatgggaagcaccacgcaatgcagatattcagaa aggatggatggttctggagtatgaacttcaatacaaagaagtaaatgaaactaaatggaaaatgatggaccctatattgacaaca tcagttccagtgtactcattgaaagtggataaggaatatgaagtgcgtgtgagatccaaacaacgaaactctggaaattatggcg agttcagtgaggtgctctatgtaacacttcctcagatgagccaatttacatgtgaagaagatttctac*tgataa*aagctt

Figure 8

Growth hormone
ttcccaaccattcccttatccaggcttttgacaacgctatgctccgcgcccatcgtctgcaccagctggcctttgacacctaccag
gagtttgaagaagcctatatcccaaaggaacagaagtattcattcctgcagaaccccagacctccctctgtttctcagagtctat
tccgacaccctccaacagggaggaaacacaacagaaatccaacctagagctgctccgcatctccctgctgctcatccagtcgt
ggctggagcccgtgcagttcctcaggagtgtcttcgccaacagcctggtgtacggcgcctctgacagcaacgtctatgacctc
ctaaaggacctagaggaaggcatccaaacgctgatggggaggctggaagatggcagcccccggactgggcagatcttcaa
gcagacctacagcaagttcgacacaaactcacacaacgatgacgcactactcaagaactacgggctgctctactgcttcagga
aggacatggacaaggtcgagacattcctgcgcatcgtgcagtgccgctctgtggagggcagctgtggcttcggcggccgc

Linker
<u>ggtggcggaggtagtggtggcggaggtagcggtggcggaggttctggtggcggaggttcc</u>

Growth hormone receptor :N-terminal SD100
Gaattcttttctggaagtgaggccacagcagctatccttagcagagcaccctggagtctgcaaagtgttaatccaggcctaaa
gacaaattcttctaaggagcctaaattcaccaagtgccgttcacctgagcgagagacttttcatgccactggacagatgaggttc
atcatggtacaaagaacctaggacccatacagctgttctataccagaaggaacactcaagaatggactcaagaatggaaagaa
tgccctgattatgtttctgctggggaaaacagctgttactttaattcatcgtttacctccatctggatacttattgtatcaagctaacta
gcaatggtggtacagtggatgaaaagtgtttctctgttgat

C-terminal SD100
Gaaatagtgcaaccagatccacccattgccctcaactggactttactgaacgtcagtttaactgggattcatgcagatatccaag
tgagatgggaagcaccacgcaatgcagatattcagaaaggatggatggttctggagtatgaacttcaatacaaagaagtaaatg
aaactaaatggaaaatgatggacccctatattgacaacatcagttccagtgtactcattgaaagtggataaggaatatgaagtgcgt
gtgagatccaaacaacgaaactctggaaattatggcgagttcagtgaggtgctctatgtaacacttcctcagatgagccaattac
atgtgaagaagatttctac*tgataa*aagctt

Figure 9

Growth hormone gggaaagagctc<u>aaggagaaaataaa</u>*at*ggggggttctcatcatcatcatcatggtatggctagcatgactggtggaca
gcaaatgggtcgggatctgtacgacgatgacgataaggatccaaccctttcccaaccattcccttatccaggcttttgacaacg
ctatgctccgcgcccatcgtctgcaccagctggcctttgacacctaccaggagtttgaagaagcctatatcccaaaggaacaga
agtattcattcctgcagaacccccagacctccctctgtttctcagagtctattccgacaccctccaacagggaggaaacacaaca
gaaatccaacctagagctgctccgcatctccctgctgctcatccagtcgtggctggagcccgtgcagttcctcaggagtgtcttc
gccaacagcctggtgtacggcgcctctgacagcaacgtctatgacctcctaaaggacctagaggaaggcatccaaacgctga
tggggaggctggaagatggcagcccccggactgggcagatcttcaagcagacctacagcaagttcgacacaaactcacaca
acgatgacgcactactcaagaactacgggctgctctactgcttcaggaaggacatggacaaggtcgagacattcctgcgcatc
gtgcagtgccgctctgtggagggcagctgtggcttcggcggccgc

Linker ggtggcggaggtagtggtggcggaggtagcggtggcggaggttctggtggcggaggttcc

Growth hormone receptor gaattcgaaatagtgcaaccagatccacccattgccctcaactggactttactgaacgtcagtttaactgggattcatgcagatat
ccaagtgagatgggaagcaccacgcaatgcagatattcagaaaggatggatggttctggagtatgaacttcaatacaaagaag
taaatgaaactaaatggaaaatgatggaccctatattgacaacatcagttccagtgtactcattgaaagtggataaggaatatgaa
gtgcgtgtgagatccaaacaacgaaactctggaaattatggcgagttcagtgaggtgctctatgtaacacttcctcagatgagcc
aatttacatgtgaagaagatttctac*tgataa*aagcttgggaaa

Figure 10 gagctc<u>aaggagaaaataaa</u>a*tg*ggggttctcatcatcatcatcatcatggtatggctagcatgactggtggacagcaaat
gggtcgggatctgtacgacgatgacgataaggatccaaccctttcccaaccattcccttatccaggcttttgacaacgctatgc
tccgcgcccatcgtctgcaccagctggcctttgacacctaccaggagtttgaagaagcctatatcccaaaggaacagaagtatt
cattcctgcagaaccccagacctccctctgtttctcagagtctattccgacaccctccaacagggaggaaacacaacagaaat
ccaacctagagctgctccgcatctccctgctgctcatccagtcgtggctggagcccgtgcagttcctcaggagtgtcttcgccaa
cagcctggtgtacggcgcctctgacagcaacgtctatgacctcctaaaggacctagaggaaggcatccaaacgctgatgggg
aggctggaagatggcagcccccggactgggcagatcttcaagcagacctacagcaagttcgacacaaactcacacaacgat
gacgcactactcaagaactacgggctgctctactgcttcaggaaggacatggacaaggtcgagacattcctgcgcatcgtgca
gtgccgctctgtggagggcagctgtggcttcggcggccgc<u>*tgataa*</u>aagggcgaattcaattcgaagcttggc

Figure 11

A gagctcaaggagaaaataaaa*tg*ggggggttctcatcatcatcatcatcatggtatggctagcatgactggtggacagcaaat
gggtcgggatctgtacgacgatgacgataaggatccaacccttttcccaaccattcccttatccaggcttttgacaacgctatgc
tccgcgcccatcgtctgcaccagctggcctttgacacctaccaggagtttgaagaagcctatatcccaaaggaacagaagtatt
cattcctgcagaaccccagacctccctctgtttctcagagtctattccgacaccctccaacagggaggaaacacaacagaaat
ccaacctagagctgctccgcatctccctgctgctcatccagtcgtggctggagcccgtgcagttcctcaggagtgtcttcgccaa
cagcctggtgtacggcgcctctgacagcaacgtctatgacctcctaaaggacctagaggaaggcatccaaacgctgatgggg
aggctggaagatggcagcccccggactgggcagatcttcaagcagacctacagcaagttcgacacaaactcacacaacgat
gacgcactactcaagaactacgggctgctctactgcttcaggaaggacatggacaaggtcgagacattcctgcgcatcgtgca
gtgccgctctgtggagggcagctgtggcttcggcggccgc*tgataa*aagggcgaattcaattcgaagcttggc

B

```
 1    VPPGEDSK DVAAPHRQPL TSSERIDKQI RYILDGISAL RKETCNKSNM
51    CESSKEALAE NNLNLPKMAE KDGCFQSGFN EETCLVKIIT GLLEFEVYLE
101   YLQNRFESSE EQARAVQMST KVLIQFLQKK AKNLDAITTP DPTTNASLLT
151   KLQAQNQWLQ DMTTHLILRS FKEFLQSSLR ALRQMGGR** VDKG
```

Figure 12 gaacttcta gatccatgtg gttatatcag tcctgaatct ccagttgtac aacttcattc taatttcact gcagtttgtg tgctaaagga aaaatgtatg gattattttc atgtaaatgc taattacatt gtctggaaaa caaaccattt tactattcct aaggagcaat atactatcat aaacagaaca gcatccagtg tcacctttac agatatagct tcattaaata ttcagctcac ttgcaacatt cttacattcg gacagcttga acagaatgtt tatggaatca caataatttc aggcttgcct ccagaaaaac ctaaaaattt gagttgcatt gtgaacgagg ggaagaaaat gaggtgtgag tgggatggtg gaagggaaac acacttggag acaaacttca ctttaaaatc tgaatgggca acacacaagt ttgctgattg caaagcaaaa cgtgacaccc ccacctcatg cactgttgat tattctactg tgtattttgt caacattgaa gtctgggtag aagcagagaa tgcccttggg aaggttacat cagatcatat caattttgat cctgtatata aagtgaagcc caatccgcca cataatttat cagtgatcaa ctcagaggaa ctgtctagta tcttaaaatt gacatggacc aacccaagta ttaagagtgt tataatacta aaatataaca ttcaatatag gaccaaagat gcctcaactt ggagccagat tcctcctgaa gacacagcat ccacccgatc ttcattcact gtccaagacc ttaaaccttt tacagaatat gtgtttagga ttcgctgtat gaaggaagat ggtaagggat actggagtga ctggagtgaa gaagcaagtg ggatcaccta tgaagataga ccatctaaag caccaagttt ctggtataaa atagatccat cccatactca aggctacaga actgtacaac tcgtgtggaa gacattgcct cctttgaag ccaatggaaa aatcttggat tatgaagtga ctctcacaag atggaaatca catttacaaa attacacagt taatgccaca aaactgacag taaatctcac aaatgatcgc tatctagcaa ccctaacagt aagaaatctt gttggcaaat cagatgcagc tgtttaact atccctgcct gtgactttca agctactcac cctgtaatgg atcttaaagc attcccccaaa gataacatgc tttgggtgga atggactact ccaagggaat ctgtaaagaa atatatactt gagtggtgtg tgttatcaga taaagcaccc tgtatcacag actggcaaca agaagatggt accgtgcatc gcacctattt aagagggaac ttagcagaga gcaaatgcta tttgataaca gttactccag tatatgctga tggaccagga agccctgaat ccataaaggc ataccttaaa caagctccac cttccaaagg acctactgtt cggacaaaaa aagtagggaa aaacgaagct gtcttagagt gggaccaact tcctgttgat gttcagaatg gatttatcag aaattatact atattttata gaaccatcat tggaaatgaa actgctgtga atgtggattc ttcccacaca gaatatacat tgtcctcttt gactagtgac acattgtaca tggtacgaat ggcagcatac acagatgaag gtgggaagga tggtccagaa ttcactttta ctaccccaaa gtttgct caa ggagaaattg aa

Figure 13

```
  1    VPPGEDSKDV AAPHRQPLTS SERIDKQIRY ILDGISALRK ETCNKSNMCE
 51    SSKEALAENN LNLPKMAEKD GCFQSGFNEE TCLVKIITGL LEFEVYLEYL
101    QNRFESSEEQ ARAVQMSTKV LIQFLQKKAK NLDAITTPDP TTNASLLTKL
151    QAQNQWLQDM TTHLILRSFK EFLQSSLRAL RQMGGRGGGG SGGGGSGGGG
201    SGGGGSVDEL LDPCGYISPE SPVVQLHSNF TAVCVLKEKC MDYFHVNANY
251    IVWKTNHFTI PKEQYTIINR TASSVTFTDI ASLNIQLTCN ILTFGQLEQN
301    VYGITIISGL PPEKPKNLSC IVNEGKKMRC EWDGGRETHL ETNFTLKSEW
351    ATHKFADCKA KRDTPTSCTV DYSTVYFVNI EVWVEAENAL GKVTSDHINF
401    DPVYKVKPNP PHNLSVINSE ELSSILKLTW TNPSIKSVII LKYNIQYRTK
451    DASTWSQIPP EDTASTRSSF TVQDLKPFTE YVFRIRCMKE DGKGYWSDWS
501    EEASGITYED RPSKAPSFWY KIDPSHTQGY RTVQLVWKTL PPFEANGKIL
551    DYEVTLTRWK SHLQNYTVNA TKLTVNLTND RYLATLTVRN LVGKSDAAVL
601    TIPACDFQAT HPVMDLKAFP KDNMLWVEWT TPRESVKKYI LEWCVLSDKA
651    PCITDWQQED GTVHRTYLRG NLAESKCYLI TVTPVYADGP GSPESIKAYL
701    KQAPPSKGPT VRTKKVGKNE AVLEWDQLPV DVQNGFIRNY TIFYRTIIGN
751    ETAVNVDSSH TEYTLSSLTS DTLYMVRMAA YTDEGGKDGP EFTFTTPKFA
801    QGEIE**KL
```

Figure 14 atttcaggcttgcctccagaaaaaacctaaaaatttgagttgcattgtgaacgaggggaagaaaatgaggtgtgagtgggatggt
ggaagggaaacacacttggagacaaacttcactttaaaatctgaatgggcaacacacaagtttgctgattgcaaagcaaaacgt
gacaccccccacctcatgcactgttgattattctactgtgtattttgtcaacattgaagtctgggtagaagcagagaatgcccttggg
aaggttacatcagatcatatcaattttgatcctgtatataaagtgaagcccaatccgccacataatttatcagtgatcaactcagag
gaactgtctagtatcttaaaattgacatggaccaacccaagtattaagagtgttataatactaaaatataacattcaatataggacca
aagatgcctcaacttggagccagattcctcctgaagacacagcatccacccgatcttcattcactgtccaagaccttaaacctttt
acagaatatgtgtttaggattcgctgtatgaaggaagatggtaagggatactggagtgactggagtgaagaagcaagtgggat
cacctatgaagatagaccatctaaagcaccaagtttctggtataaaatagatccatcccatactcaaggctacagaactgtacaa
ctcgtgtggaagacattgcctcctttgaagccaatggaaaaatcttggattatgaagtgactctcacaagatggaaatcacattta
caaaattacacagttaatgccacaaaactgacagtaaatctcacaaatgatcgctatctagcaaccctaacagtaagaaatcttgt
tggcaaatcagatgcagctgttttaactatccctgcctgtgactttcaagctactcaccctgtaatggatcttaaagcattccccaaa
gataacatgctttgggtggaatggactactccaagggaatctgtaaagaaatatatacttgagtggtgtgtgttatcagataaagc
accctgtatcacagactggcaacaagaagatggtaccgtgcatcgcacctatttaagagggaacttagcagagagcaaatgct
atttgataacagttactccagtatatgctgatggaccaggaagccctgaatccataaaggcataccttaaacaagctccaccttcc
aaaggacctactgttcggacaaaaaaagtagggaaaaacgaagctgtcttagagtgggaccaacttcctgttgatgttcagaat
ggatttatcagaaattatactatatttatagaaccatcattggaaatgaaactgctgtgaatgtggattcttcccacacagaatatac
attgtcctctttgactagtgacacattgtacatggtacgaatggcagcatacacagatgaaggtgggaaggatggtccagaattc
acttttactaccccaaagtttgct caaggagaaattgaa

Figure 15 aatccgccacataatttatcagtgatcaactcagaggaactgtctagtatcttaaaattgacatggaccaacccaagtattaagagt
gttataatactaaaatataacattcaatataggaccaaagatgcctcaacttggagccagattcctcctgaagacacagcatccac
ccgatcttcattcactgtccaagaccttaaaccttttacagaatatgtgtttaggattcgctgtatgaaggaagatggtaagggata
ctggagtgactggagtgaagaagcaagtgggatcacctatgaagatagaccatctaaagcaccaagtttctggtataaaataga
tccatcccatactcaaggctacagaactgtacaactcgtgtggaagacattgcctcctttgaagccaatggaaaaatcttggatt
atgaagtgactctcacaagatggaaatcacatttacaaaattacacagttaatgccacaaaactgacagtaaatctcacaaatgat
cgctatctagcaaccctaacagtaagaaatcttgttggcaaatcagatgcagctgttttaactatccctgcctgtgactttcaagcta
ctcaccctgtaatggatcttaaagcattccccaaagataacatgctttgggtggaatggactactccaagggaatctgtaaagaa
atatatacttgagtggtgtgtgttatcagataaagcacccigtatcacagactggcaacaagaagatggtaccgtgcatcgcacc
tatttaagagggaacttagcagagagcaaatgctatttgataacagttactccagtatatgctgatggaccaggaagccctgaat
ccataaaggcatac cttaaacaagctccaccttccaaaggacctactgttcggacaaaaaaagtagggaaaaacgaagctgtc
ttagagtgggaccaacttcctgttgatgttcagaatggatttatcagaaattatactatatttatagaaccatcattggaaatgaaac
tgctgtgaatgtggattcttcccacacagaatatacattgtcctctttgactagtgacacattgtacatggtacgaatggcagcatac
acagatgaaggtgggaaggatggtccagaattcacttttactaccccaaagtttgctcaaggagaaattgaa

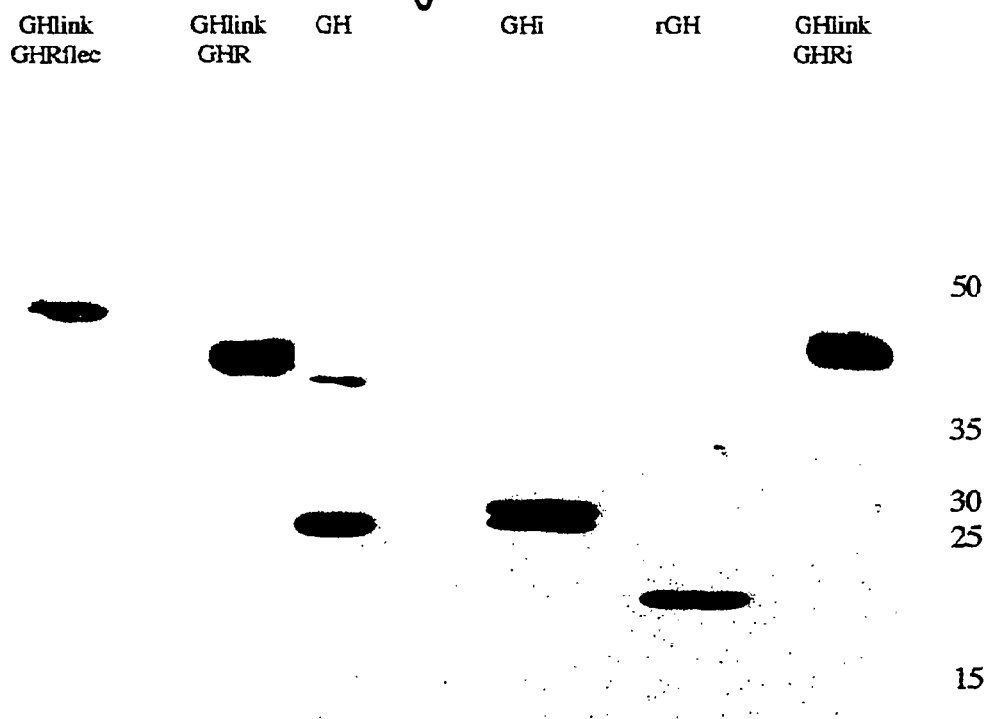

Figure 16.

Sample description:

GHlinkGHRflec: pTrcHisGHlinkGHRflec, contains full length extracellular domain of growth hormone receptor (IPTG induced).

GHlinkGHR: pTrcHisGhlinkGHR, contains only C-terminal SD100 of growth hormone receptor (IPTG induced)

GH: pTrcHisGHstop, contains full length growth hormone (IPTG induced)

GHi: pJonexGHstop, contains full length GH (heat induced)

RGH: purified recombinant human growth hormone

GHlinkGHRi: pJonexGHlinkGHR, contains full length GhlinkGHR (heat induced)

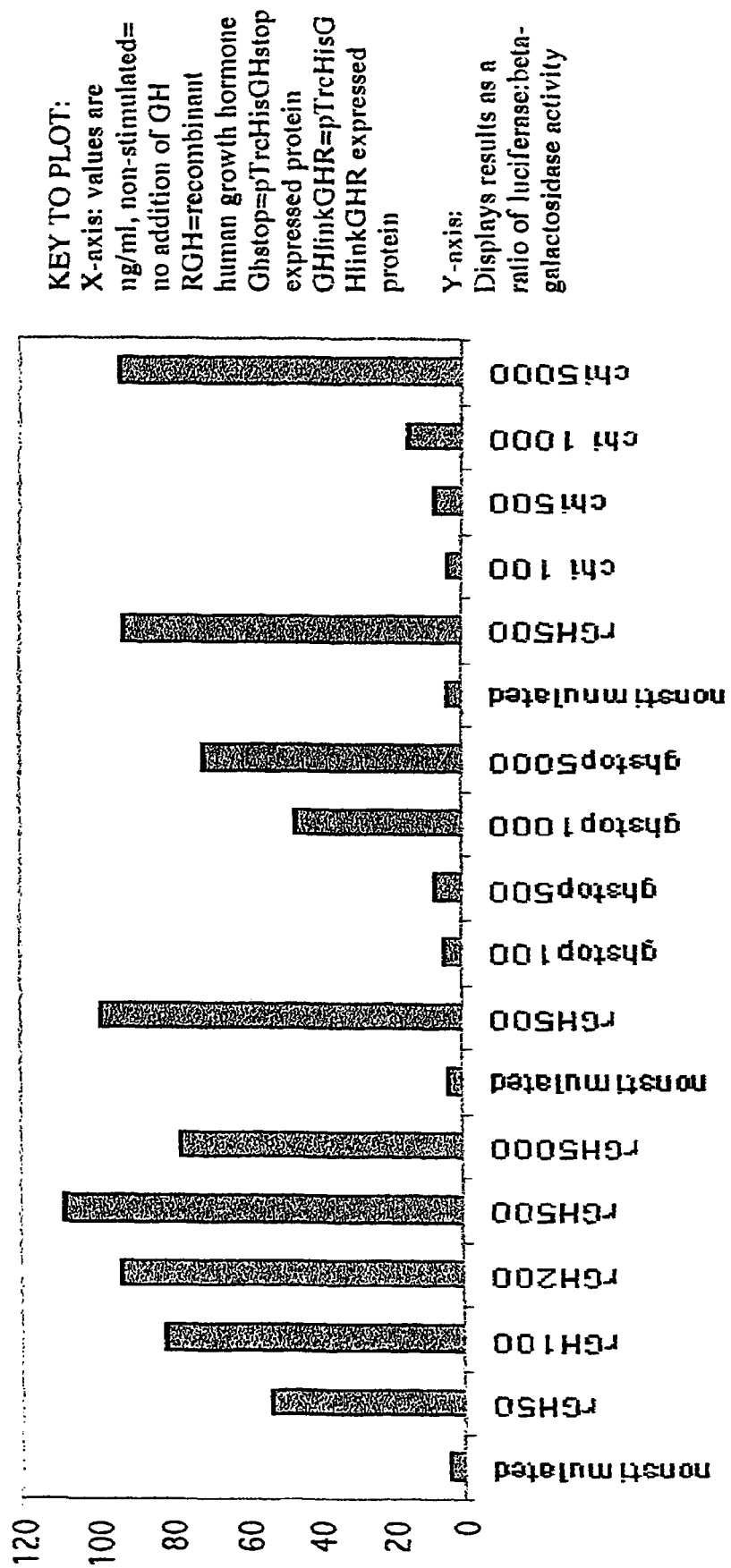
Figure 17A: Reporter gene assay for His-tag purified Ghstop and GHlinkGHR.

Figure 17B: Reporter gene assay: Table of results obtained for His-tag purified Ghstop and GHlinkGHR

| Sample | Activity ratio | Standard error | Fold induction |
|---|---|---|---|
| Non stimulated | 4.54 | 0.3 | 1 |
| rGH 50 | 53.73 | 1.46 | 11.8 |
| rGH 100 | 82.08 | 3.3 | 18.1 |
| rGH 200 | 93.65 | 5.57 | 20.6 |
| rGH 500 | 108.54 | 5.02 | 23.9 |
| rGH 5000 | 76.93 | 13.37 | 16.9 |
|  |  |  |  |
| Non stimulated | 4.61 | 0.6 | 1 |
| rGh 50 | 98.61 | 7.9 | 21.4 |
| Ghstop 100 | 5.36 | 0.05 | 1.2 |
| Ghstop 500 | 8.44 | 1.3 | 1.8 |
| Ghstop 1000 | 45.92 | 0.56 | 10 |
| Ghstop 5000 | 71.24 | 6.89 | 15.4 |
|  |  |  |  |
| Non stimulated | 4.38 | 0.91 | 1 |
| rGH 100 | 92.76 | 0.92 | 21.1 |
| Chi 500 | 8.12 | 2.82 | 1.85 |
| Chi 1000 | 15.18 | 16 | 3.46 |
| Chi 5000 |  |  |  |
|  |  |  |  |

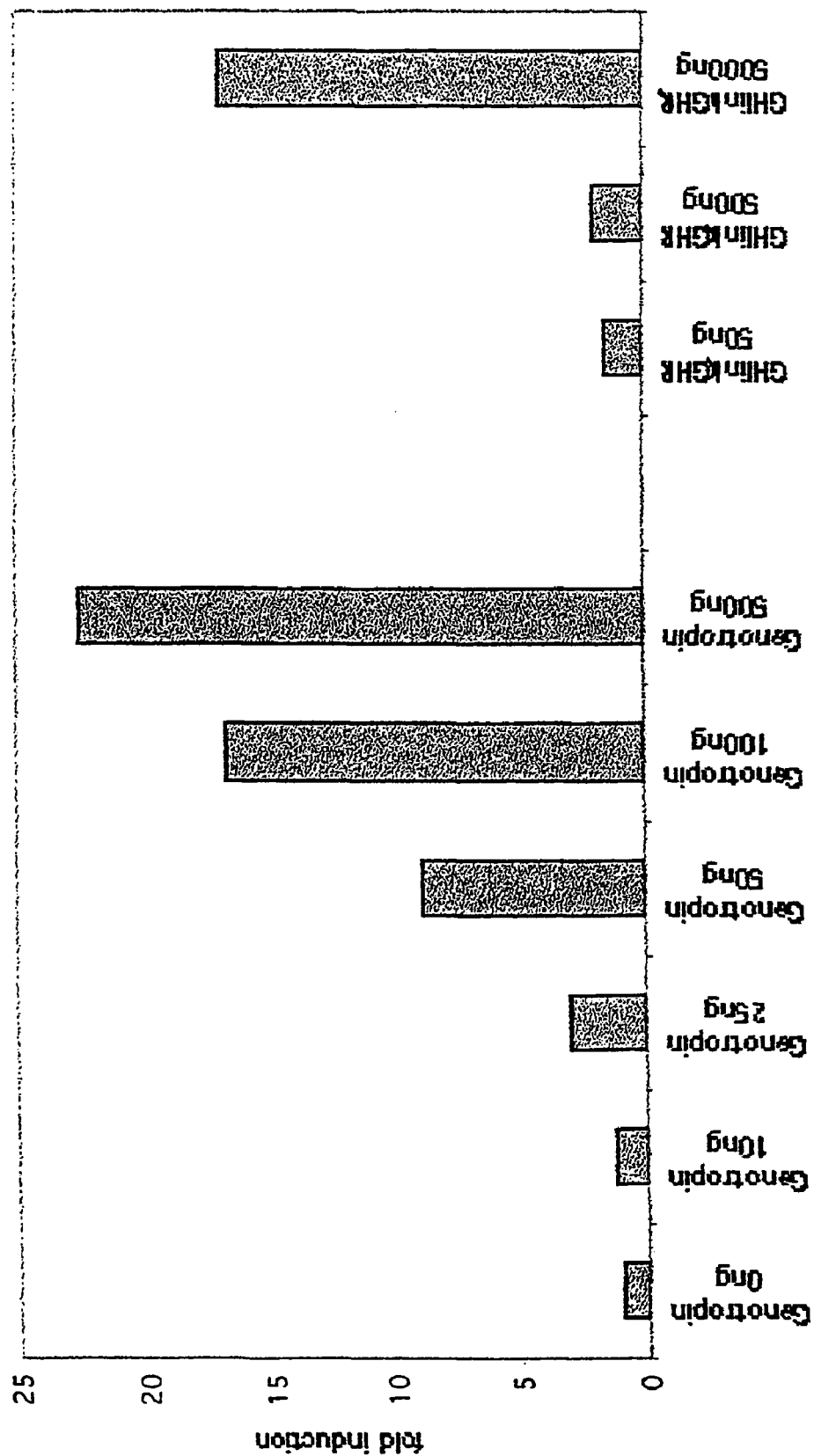
Figure 19: Bioassay of GH showing dose response for genotropin and GHlinkGHR

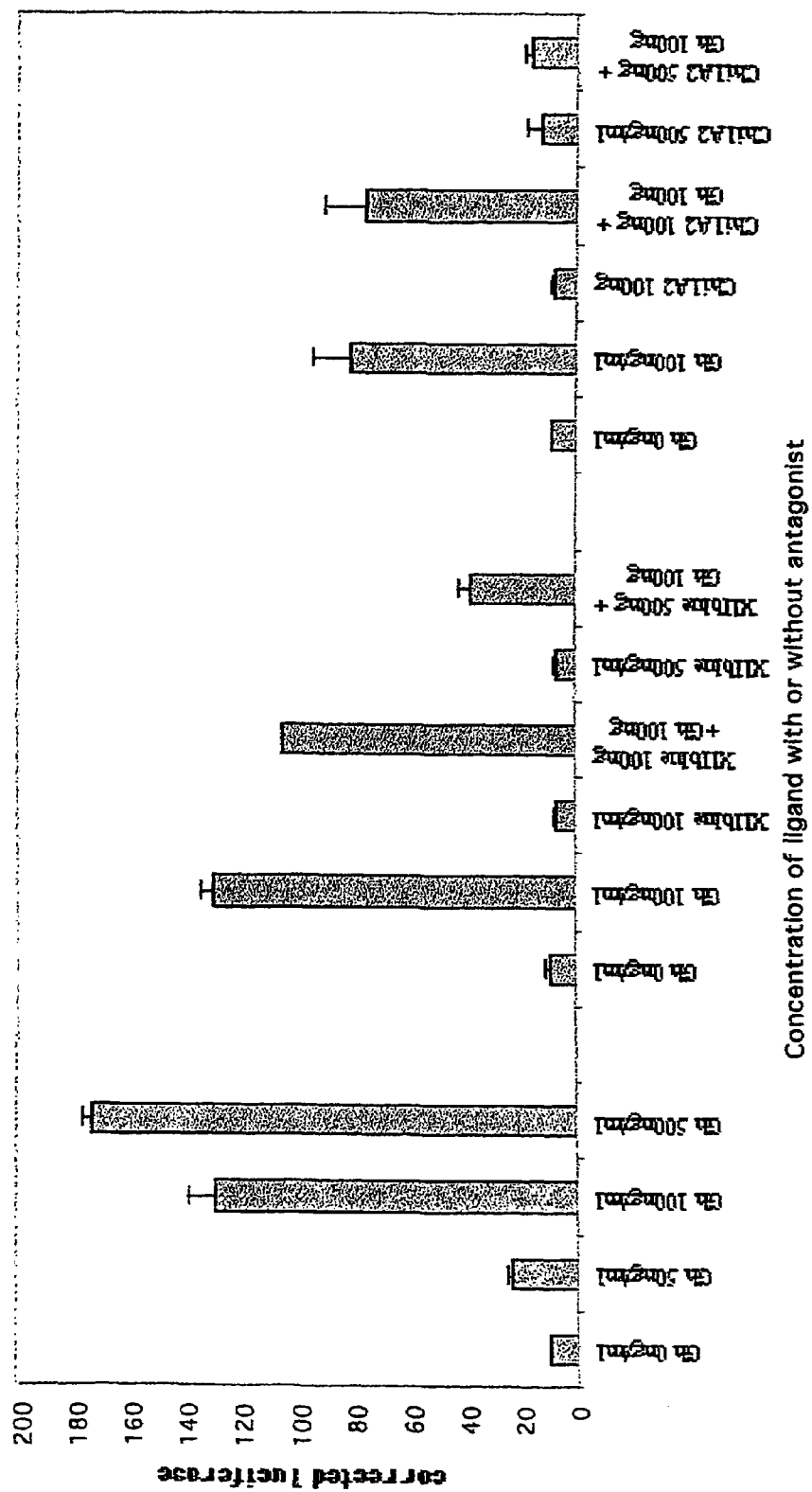

Figure 21: The chimera 1A2 was generated using the phagemid method to remove the linker sequence from GHlinkGHR and generate a fusion protein of the C-terminus of growth hormone directly the N-terminus of the GHR SD100. The DNA sequence is given below (GH in bold and GHR SD100 in italics)

**ttcccaaccattcccttatccaggcttttgacaacgctatgctccgcgcccatcgtctgcaccagctggcctttgacacctaccaggagtttga
agaagcctatatcccaaaggaacagaagtattcattcctgcagaaccccagacctccctctgtttctcagagtctattccgacaccctccaa
cagggaggaaacacaacagaaatccaacctagagctgctccgcatctccctgctgctcatccagtcgtggctggagcccgtgcagttcctca
ggagtgtcttcgccaacagcctggtgtacggcgcctctgacagcaacgtctatgacctcctaaaggacctagaggaaggcatccaaacgct
gatggggaggctggaagatggcagcccccggactgggcagatcttcaagcagacctacagcaagttcgacacaaactcacacaacgatg
acgcactactcaagaactacgggctgctctactgcttcaggaaggacatggacaaggtcgagacattcctgcgcatcgtgcagtgccgctct
gtggagggcagctgtggcttcgaaata**_gtgcaaccagatccaccccattgccctcaactggactttactgaacgtcagtttaactgggattcatgc
agatatccaagtgagatgggaagcaccacgcaatgcagatattcagaaaggatggatggttctggagtatgaacttcaatacaaagaagtaa
atgaaactaaatggaaaatgatggaccctatattgacaacatcagttccagtgtactcattgaaagtggataaggaatatgaagtgcgtgtgaga
tccaaacaacgaaactctggaaattatggcgagttcagtgaggtgctctatgtaacacttcctcagatgagccaatttacatgtgaagaagatttct
actgataaaagctt_

Figure 22: Protein sequence of Chi 1A2 (311 amino acids)

```
Fptiplsrlfdnamlrahrlhqlafdtyqefeeayipkeqkysflqnpqtslcfsesiptp
snreetqqksnlellrislllliqswlepvqflrsvfanslvygasdsnvydllkdleegiq
tlmgrledgsprtgqifkqtyskfdtnshnddallknygllycfrkdmdkvetflrivqcr
svegscgfeivqpdppialnwtllnvsltgihadiqvrweaprnadiqkgwmvleyelqyk
evnetkwkmmdpilttsvpvyslkvdkeyevrvrskqrnsgnygefsevlyvtlpqmsqft
ceedfy**kl
```

FUSION PROTEIN COMPRISING GROWTH HORMONE AND GROWTH HORMONE RECEPTOR

FIELD OF THE INVENTION

This invention relates to agents which bind to cell surface receptors; methods to manufacture said agents; therapeutic compositions comprising said agents; and screening methods to identify novel agents.

BACKGROUND OF THE INVENTION

Intercellular and/or intracellular signalling via receptor mediated activation of biochemical and/or molecular mechanisms is a fundamental process for regulating cellular and/or tissue homeostasis. Typically, ligands which interact with receptors to bring about a suitable biochemical response are known as agonists and those that prevent, or hinder, a biochemical response are known as antagonists. For example, and not by way of limitation, cell specific growth factors are ligands that act as agonists and bind receptors located at the cell surface. Activation of the receptors by ligand-specific binding promotes cell proliferation via activation of intracellular signalling cascades that result in the expression of, amongst other things, cell-cycle specific genes, and the activation of quiescent cells to proliferate. Growth factors may also activate cellular differentiation.

A large group of growth factors, referred to as cytokines, are involved in a number of diverse cellular functions. These include, by example and not by way of limitation, modulation of the immune system, regulation of energy metabolism and control of growth and development. Cytokines which are secreted by lymphocytes are termed lymphokines (also known as interleukins). Those secreted by monocytes and macrophages are termed monokines. Cytokines are also secreted by endocrine glands, (for example growth hormone (GH) by the pituitary gland), and adipose cells (for example leptin). Cytokines mediate their effects via receptors expressed at the cell surface on target cells.

Receptors of the cytokine receptor family possess a single transmembrane domain and lack intrinsic enzyme activity (1). Upon the binding of a cytokine to a cognate receptor, either receptor homo- or hetero-dimerisation or oligomerisation occurs. The receptor complex is internalised and signalling occurs through the activation of associated signalling cascades that include the Jak/Stat and Mapk pathways. Internalisation is followed by a recycling step whereby the receptor molecule is regenerated for further use within the cell.

The study of receptor/ligand interactions has been facilitated by the ability to define the structures of receptor molecules and their ligands. Several approaches, including X-ray crystallography and computer modelling, have greatly facilitated our understanding of the biology of ligand: receptor binding.

An example of the above is described with respect to GH and its binding to the growth hormone receptor (GHR). This example is merely meant to be illustrative and not limiting and is an example of a cytokine which activates a signal transduction cascade by binding, dimerisation and internalisation of the receptor:ligand complex.

It is known that a single molecule of growth hormone (GM) associates with two receptor molecules (3-6). This occurs through two unique receptor-binding sites on GH and a common binding pocket on the extracellular domain of two receptors. Site 1 on the GH molecule has a higher affinity than site 2, and receptor dimerization is thought to occur sequentially with one receptor binding to site 1 on GH followed by recruitment of a second receptor to site 2.

The extracellular domain of the GHR exists as two linked domains each of approximately 100 amino acids (SD-100), the C-terminal SD-100 domain being closest to the cell surface and the N-terminal SD-100 domain being furthest away. It is a conformational change in these two domains that occurs on hormone binding with the formation of the trimeric complex GHR-GH-GHR (FIG. 5). It has been proposed that ligand-driven receptor dimerization is the key event leading to signal activation (3), triggering phosphorylation cascades that include the Jak2/Stat5 pathway (7). Using confocal microscopy and Frequency Resonance Energy Transfer (FRET) it is known that there is very rapid internalisation of GHR after ligand binding and that internalisation and signalling are independent functions (16). Internalisation of the GHR-GH-GHR complex is followed by a recycling step whereby the receptor molecule is regenerated for further use within the cell.

The importance of receptor dimerization in signal transduction is indicated by a number of experiments. High concentrations of GH, which favour the monomeric GH-GHR complex, inhibit the GH signal (8). Mutations in the inter-receptor dimerization domain inhibit signalling without influencing GH binding (10). The strongest evidence comes from work with a GH molecule mutated at site 2 to prevent receptor dimerisation. These GH mutants block GH-stimulated cell proliferation (8, 11-14), the conformational change associated with receptor dimerization (15), and Jak-Stat signalling (16).

U.S. Pat. No. 5,849,535 describes a human growth hormone including a number of amino acid substitutions which disrupt Site 2 binding. The substitution of a different amino acid at G120 is one modification that disrupts Site 2 binding and the hGH variant acts as an hGH antagonist.

The in vivo efficacy of hGH and hGH variants is determined, in part, by their affinity for the hGH receptor and rate of clearance from the circulation. The kidneys are relatively small organs which receive approximately 25% of cardiac output. The kidneys perform several important functions primarily related to the regulation of the composition and volume of body fluids. The kidneys filter about 100 litres of plasma every day and of the blood flow in and out of a kidney only approximately 1% becomes urine. Approximately 20% of the plasma that passes through the kidney gets filtered into the nephron. Filtration takes place in the glomerulus which is driven by the hydrostatic pressure of the blood. Water and small molecules are filtered whereas blood cells and large molecules, for example polypeptides, do not pass through the glomerular filter.

Those polypeptides with an effective molecular weight above 70 kDa are not cleared by glomerular filtration because they are simply too large to be filtered. Certain proteins of small molecular weight are filtered by the glomerulus and are found in the urine. For example, Growth Hormone (GH has a molecular weight of 22.1 kDa and the kidney is responsible for clearing up to 60-70% of GH in humans (Baumann, 1991; Haffner et al, 1994), and up to 67% in rat (Johnson & Maack, 1977). Other examples of relatively small molecular weight polypeptides which are filtered by the kidney include lepin, erythropoeitin, and IL-6.

Syed et al (1997) constructed an anti-coagulant fusion protein which fused hirudin with albumin. This fusion protein showed extended plasma half life whilst maintaining a potent anti-thrombin (anti-coagulant) activity. This is likely to result from decrease in glomerular filtration by the kidneys. However a problem associated with this strategy is that hirudin is a foreign protein and which is known to provoke a strong immune response. The increase in molecular weight of the hirudin fusion protein increases the catabolic half-life from 0.7 hours to 4.6 days.

A further method to increase the effective molecular weight of proteins and to produce a product which has reduced immunogenicity is to coat the protein in polyethylene glycol (EG). The in-vivo half-life of GH has been increased by conjugating the proteins with poly ethylene glycol, which is termed "pegylation" (See Abuchowski et al., *J. Biol Chem.*, 252:3582-3586 (1977). PEG is typically characterised as a non-immunogenic uncharged polymer with three water molecules per ethylene oxide monomer. PEG is believed to slow renal clearance by providing increased hydrodynamic volume in pegylated proteins (Maxfield et al., *Polymer*, 16:505-509 (1975)). U.S. Pat. No. 5,849,535 also describes humanGH (hGH) variants which are conjugated to one or more polyols, such as poly(ethylene glycol) (PEG).

An alternative to pegylation which provides a molecule which retains biological activity and is immune silent is herein disclosed. A chimeric protein comprising the extracelluar domain, or part thereof, of a receptor linked, via a variable flexible linker molecule to its cognate ligand to produce an agent with an apparent molecular weight greater than the native ligand. In the example provided, GH is fused to at least part of the growth hormone receptor (GHR) which gives an approximate molecular weight of 55 kDa which when glycosylated increases the effective molecular weight to approximately 75 kDa This would be of sufficient size to prevent the chimera being filtered by the kidney and, importantly, the molecule retains biological activity.

A long-acting form of growth hormone could be used in the treatment of both childhood and adult onset growth hormone deficiency. Growth hormone has well known anabolic actions and a long-acting form of growth hormone could be used for the treatment of a number of conditions by virtue of its anabolic actions including promoting growth in Turner's syndrome, renal failure, osteoporosis and muscle wasting in catabolic patients. Bovine somatotropin is currently used to enhance milk production from cows. A long-acting form of growth hormone would be an effective treatment for increasing milk yield from cows (Peel et al. 1981).

This strategy is applicable to other ligand-receptor combinations (eg. leptin, erythropoeitin and IL-6). For example, leptin is being trialed as a therapy for obesity (Mantzoros & Flier, 2000). A long-acting form of leptin could be used to treat obesity, insulin resistance, hyperlipidaemia and hypertension. Erythropoeitin is important in the generation of red cell mass. A long-acting form of erythropoeitin could be used to treat anaemia especially that associated with renal failure.

Truncated GH receptors, which lack the cytoplasmic domain of the receptor, act as dominant negative inhibitors of GH signalling (9,19). The truncated receptor is expressed at a high level on the cell surface because it lacks the cytoplasmic domain essential for internalisation (16). In the presence of GH, the truncated receptor heterodimerises with the fill length receptor and blocks signalling because it lacks the cytoplasmic domain. As the truncated receptor fails to internalise it acts as a dominant negative inhibitor preventing internalisation of the GH receptor complex.

The disorders of acromegaly and gigantism result from an excess of growth hormone, usually due to pituitary tumours. A drug currently under trial is the pegylated GH antagonist B2036, designed using recently acquired knowledge of the molecular structure of the growth hormone receptor (GHR). Unfortunately, high levels of B2036 are required to antagonise GH action with drug levels over a 1000 times higher than endogenous GH levels (18).

B2036, despite having a mutated site 2, binds to a receptor dimer, and is internalised in an identical fashion to GH. It does not however trigger the conformational change required for signalling. The high dose requirement of the antagonist relates to its internalisation and its differential binding to soluble and membrane bound receptor. The pegylated antagonist does not bind efficiently to membrane bound receptor although pegylation increases half-life and lowers immunogenicity. The non-pegylated antagonist is rapidly internalised and cleared.

There is a need to provide an antagonist that is not internalised by the cell and that can be delivered in lower doses. This would prove a more effective and potent antagonist and provide a more effective and economical treatment.

The leptin receptor (28) and erythropoietin (EPO) receptor (29,30) share considerable structural homology to the GHR and require a similar dimerisation process to trigger signalling. Leptin supresses appetite and leptin resistance is associated with obesity. A leptin receptor antagonist will provide a treatment for anorexia nervosa. EPO excess causes polycythaemia which may be secondary to hypoxia (chronic lung disease), or primary in the case of polycythaemia rubra vera (a disorder of excess red blood cells). An EPO antagonist will provide a therapy for polycythaemia.

A further example of a receptor: ligand binding is provided by the IL-6 activation of its cognate receptor. The current model for IL-6 activation of its cognate receptor stipulates that IL-6 binds to either soluble or membrane bound IL-6 receptor (IL-6R). The IL-6/UL-6R complex then recruits two molecules of gp130 and the tetramer signals through the dimerisation of the two gp130 molecules which possess cytoplasmic domains that associate with signalling molecules (Grotzinger et al., 1999). In nature UL-6 and the IL-6R exist as separate molecules which possess high affinity binding sites for each other and the association with the signal transducing molecule gp130 occurs through covalent linkage and the formation of disulfide bonds.

We have been studying receptor trafficking and binding protein production for two members of the cytokine receptor family; GH and leptin (9,16,20,21). These two hormones play a fundamental role in determining body composition in adults. Both leptin and GH are important in regulating energy expenditure, appetite, and fat mass. The ability to manipulate the biological actions of leptin and GH will have important therapeutic outcomes for the treatment of both hormone excess and deficiency.

Using confocal microscopy and Frequency Resonance Energy Transfer (FRET) we have shown that there is very rapid internalisation of GH receptor after ligand binding and that internalisation and signalling are independent functions (16). Our recent work shows that the GH antagonist, pegvisomant, despite having a mutated site 2, binds to a receptor dimer, is internalised in an identical fashion to GH, but does not trigger the conformational change required for signalling. We have demonstrated that the high dose requirement of the antagonist relates to its internalisation and its differential binding to soluble and membrane bound receptor. The pegylated antagonist does not bind efficiently to membrane bound receptor and the non-pegylated antagonist is rapidly internalised and cleared.

We demonstrate that a truncated GHE, which lacks the cytoplasmic domain of the receptor, can act as a dominant negative antagonist of GH signalling, (FIG. 5) (9,20). The truncated receptor is expressed at a high level on the cell surface as it lacks cytoplasmic domain essential for internalisation (16). The truncated receptor heterodimerises with the full length receptor, blocks signalling as it lacks the cytoplasmic domain, and acts as a dominant negative because it is present in excess on the cell surface and prevents internalization of the GH receptor complex.

There are two problems associated with using truncated receptors in the generation of antagonists to GH. A truncated receptor in the membrane would have to be generated from within the cell. The GHR is also proteolytically cleaved and in time the majority of the truncated receptor would be lost into the circulation.

We link GH, through its C-terminus and a linker, to the N-terminus of the C-terminal SD-100 domain of the GHR. By varying the length of the linker we define a molecule that has the flexibility to allow binding of GH through site 1 to full length receptor at the cell surface. The C-terminal SD-100 domain of the receptor will then rotate in to complete the trimeric structure GHR-GH-GHRtr where GHRtr is the C-terminal SD-100 domain. This complex neither signals nor internalises, and effectively antagonises GH action. It has the additional advantages of low immunogenicity and low clearance as the majority of GH is cleared via the GHR (22).

We also demonstrate that the leptin receptor produces a soluble binding protein (21) as do many cytokine receptors (2), and the predominant peripheral form of the leptin receptor is a truncated receptor similar to the truncated GHR (27, 28). Our recent work has demonstrated that truncated leptin receptors can inhibit leptin signalling. The erythropoietin (EPO) receptor shares a very similar crystal structure to GHR and an EPO chimera with the C-terminal SD100 of the EPO receptor would function as an antagonist.

STATEMENTS OF INVENTION

According to the present invention there is provided a binding agent comprising a first part capable of binding a ligand binding domain of a receptor linked to a second part comprising a receptor binding domain wherein said binding agent modulates the activity of the receptor.

In one embodiment of the invention, the binding agent antagonises the activity of the receptor.

In an alternative embodiment of the invention, the binding agent agonises the activity of the receptor.

Preferably the first part comprises a cytokine or the binding domain of a cytokine.

More preferably still the first part comprises a cytokine or the binding domain of a cytokine selected from the following: growth hormone; leptin; erythropoietin; prolactin; TNF, interleukins (IL), IL-2, IL-3, IL-4, IL-5, IL-6, IL-7, IL-9, IL-10, IL-11; the p35 subunit of IL-12, IL-13, IL-15; granulocyte colony stimulating factor (G-CSF); granulocyte macrophage colony stimulating factor (GM-CSF); ciliary neurotrophic factor (CNTF); cardiotrophin-I (CT-I); leukemia inhibitory factor (LIF); oncostatin M (OSM); interferon, IFNα and IFNγ.

Preferably the second part of the binding agent comprises at least part of the cognate receptor of the cytokine or a part of an associated receptor.

Preferably the first part is GH.

Preferably the second part is one extracellular domain of GHR. More preferably the second part is the C-terminal SD-100 domain of GHR.

In an alternative embodiment the first part is IL-6 or a binding domain of IL-6 and the second part is a part of gp 130.

An embodiment of the invention exploits the high affinity of a cytokine for its receptor and the failure of truncated receptors to internalise to generate a specific receptor antagonist which is a chimera of the cytokine and its cognate receptor. The binding agent of the invention has the important advantage that binding of the cytokine to its receptor does not trigger internalisation of the receptor-cytokine complex. This means that dosage of the antagonist can be minimised.

In one embodiment of the invention, the binding agent is a fusion protein.

In an alternative embodiment of the invention, the first part is linked by a linker to the second part. The linker may be flexible.

The linker could be at any residue within the extracellular domain of the receptor which would allow growth hormone to flexibly bind with the free receptor at the cell surface. Where the first part is GH and the second part is one extracellular domain of GHR, the linkage may be made between any peptide residue in the GH and GHR. Preferably the linkage is made between a residue close to the C-terminus of the GH molecule and a residue close to the N-terminus of the GHR. More preferably the linkage is made between a residue close to the C-terminus of the GH molecule and a residue close to the N-terminal of the N-terminal of the C-terminal SD-100. More preferably the linkage is made at any of residues 126-128 of the N-terminus of the C-terminal SD-100 of the GHR. In one embodiment of the invention, the linkage is made at residue 127 of the N-terminus of the C-terminal SD-100. Preferably the linker is a peptide.

It will be apparent to one skilled in the art that alternative linkers can be used to link first and second parts. By way of example and by no means of limitation, suitable linkers might be a nucleic acid (eg oligonucleotide); a peptide nucleic acid; a chemical crosslinker (eg polyoxyethylene).

The crystal structure of the GHR-GH-GHR complex reveals that the distance between the C-terminus of GH (residue 191) and N-terminus of the C-terminus SD-100 (residue 126-128) is 10A. This provides invaluable information with respect to linker design.

Preferably the linker is a polypeptide which comprises 5 to 30 amino acid residues. More preferably the linker comprises 10 to 20 amino acid residues.

More preferably the linker comprises at least one copy of the peptide:

Gly Gly Gly Gly Ser (hereinafter referred to as "Gly4Ser") (SEQ ID NO: 17).

In one embodiment of the invention the linker is 10 amino acids in length and comprises two copies of the Gly4Ser(SEQ ID NO: 17) linker. In an alternative embodiment of the invention, the linker is 15 amino acids in length and comprises three copies of the Gly4Ser (SEQ ID NO: 17) linker. In yet an alternative embodiment, the linker is 20 amino acids in length and comprises four copies of the Gly4Ser(SEQ ID NO: 17) linker. According to a further aspect of the invention there is provided a nucleic acid molecule comprising a nucleic acid sequence which encodes a binding agent according to the invention selected from the group consisting of:

i) the group comprising FIGS. 4, 5, 8, 9 and 21;
ii) nucleic acids which hybridise to the sequences of (i) above and which have receptor modulating activity; and
iii) nucleic acid sequences which are degenerate as a result of the genetic code to the sequences defined in (i) and (ii) above.

In a preferred embodiment of the invention said nucleic acid hybridises under stringent hybridisation conditions to the sequences represented in FIGS. 4,5,8,9, or 21.

Stringent hybridisation/washing conditions are well known in the art. For example, nucleic acid hybrids that are stable after washing in 0.1×SSC,0.1% SDS at 60° C. It is well known in the art that optimal hybridisation conditions can be calculated if the sequence of the nucleic acid is known. For example, hybridisation conditions can be determined by the GC content of the nucleic acid subject to hybridisation. Please see Sambrook et al (1989) Molecular Cloning; A Laboratory Approach. A common formula for calculating the stringency conditions required to achieve hybridisation between nucleic acid molecules of a specified homology is:

$$T_m=81.5° C.+16.6 \text{ Log }[Na^+]+0.41[\% \text{ G+C}]-0.63(\% \text{ formamide}).$$

Typically, hybridisation conditions uses 4-6×SSPE (20× SSPE contains 175.3 g NaCl, 88.2 g $NaH_2PO_4H_2O$ and 7.4 g EDTA dissolved to 1 litre and the pH adjusted to 7.4); 5-10× Denhardts solution (50× Denhardts solution contains 5 g Ficoll (type 400, Pharmacia), 5 g polyvinylpyrrolidone abd 5 g bovine serum albumen/500 ml; 100 μg-1.0 mg/ml sonicated salmon/herring DNA; 0.1-1.0% sodium dodecyl sulphate; optionally 40-60% deionised formamide. Hybridisation temperature will vary depending on the GC content of the nucleic acid target sequence but will typically be between 42°-65° C.

According to a further aspect of the invention there is provided a polypeptide which is encoded by a nucleic acid molecule according to the invention.

In a preferred embodiment of the invention the polypeptide so encoded is modified by deletion, addition or substitution of at least one amino acid residue. Ideally said modification enhances the antagonistic or agonistic effects of said polypeptide with respect to the inhibition or activation of receptor mediated cell signalling.

Alternatively, or preferably, said modification includes the use of modified amino acids in the production of recombinant or synthetic forms of polypeptides.

It will be apparent to one skilled in the art that modified amino acids include, by way of example and not by way of limitation, 4-hydroxyproline, 5-hydroxylysine, $N^6$-acetyllysine, $N^6$-methyllysine, $N^6,N^6$-dimethyllysine, $N^6,N^6,N^6$-trimethyllysine, cyclohexyalanine, D-amino acids, ornithine. The incorporation of modified amino acids may confer advantageous properties on polypeptides comprising FIG. 21. For example, the incorporation of modified amino acids may increase the affinity of the polypeptide for its binding site, or the modified amino acids may confer increased in vivo stability on the polypeptide thus allowing a decrease in the effective amount of therapeutic polypeptide administered to a patient.

According to a yet further aspect of the invention there is provided a vector including a DNA molecule encoding a binding agent according to any preceding aspect or embodiment of the invention.

In a preferred embodiment of the invention said vector is provided with means to recombinantly manufacture the binding agent of the invention.

In a preferred embodiment of the invention said vector is an expression vector adapted for prokaryotic gene expression.

Prokaryotic expression systems are well known in the art and comprise vectors adapted for high level constitutive and inducible expression. Inducible expression systems are particularly advantageous if the recombinant polypeptide is toxic to the bacterial cell. Induction of expression is tightly regulated by promoters responsive to various inducers (eg IPTG inducible). Bacterial cells can be grown to stationary phase before induction thereby reducing harmful effects of toxic polypeptides.

Additionally it is also well known in the art that certain polypeptides are difficult to manufacture recombinantly due, for example, to protein instability or problems of aggregation.

It is well known that genetically modified bacterial strains are available which are mutated in genes (eg bacterial proteases) which facilitate the production of native and recombinant bacterial polypeptides.

In a further preferred embodiment of the invention said vector is an expression vector adapted for eukaryotic gene expression.

Typically said adaptation includes, by example and not by way of limitation, the provision of transcription control sequences (promoter sequences) which mediate cell/tissue specific expression. These promoter sequences may be cell/tissue specific, inducible or constitutive.

Promoter is an art recognised term and, for the sake of clarity, includes the following features which are provided by example only, and not by way of limitation. Enhancer elements are cis acting nucleic acid sequences often found 5' to the transcription initiation site of a gene (enhancers can also be found 3' to a gene sequence or even located in intronic sequences and are therefore position independent). Enhancers function to increase the rate of transcription of the gene to which the enhancer is linked. Enhancer activity is responsive to trans acting transcription factors (polypeptides) which have been shown to bind specifically to enhancer elements. The binding/activity of transcription factors (please see Eulcaryotic Transcription Factors, by David S Latchinan, Academic Press Ltd, San Diego) is responsive to a number of environmental cues which include, by example and not by way of limitation, intermediary metabolites (eg glucose, lipids), environmental effectors (eg light, heat).

Promoter elements also include so called TATA box and RNA polymerase initiation selection (RIS) sequences which function to select a site of transcription initiation. These sequences also bind polypeptides which function, inter alia, to facilitate transcription initiation selection by RNA polymerase.

Adaptations also include the provision of selectable markers and autonomous replication sequences which both facilitate the maintenance of said vector in either the eukaryotic cell or prokaryotic host. Vectors which are maintained autonomously are referred to as episomal vectors.

Adaptations which facilitate the expression of vector encoded genes include the provision of transcription termination/polyadenylation sequences. This also includes the provision of internal ribosome entry sites (IRES) which function to maximise expression of vector encoded genes arranged in bicistronic or multi-cistronic expression cassettes.

These adaptations are well known in the art. There is a significant amount of published literature with respect to expression vector construction and recombinant DNA techniques in general. Please see, Sarnbrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc.(1994).

In yet a further aspect of the invention there is provided a method to prepare a binding agent polypeptide according to the invention comprising:

(i) growing a cell transformed or transfected with a vector or nucleic acid of the present invention in conditions conducive to the manufacture of said polypeptide; and (ii) purifying said polypeptide from said cell, or its growth environment.

In a preferred method of the invention said vector encodes, and thus said recombinant polypeptide is provided with, a secretion signal to facilitate purification of said binding agent polypeptide.

In yet a further aspect of the invention there is provided a cell transformed/transfected with the vector or nucleic acid according to the invention.

Preferably said cell eukaryotic and is selected from: fungal; insect (eg *Spodoptera frugiperda*); amphibian; plant; mammalian.

More preferably said cell is prokaryotic and is an *E. coli* cell.

Preferably the binding agent of the present invention is used for the manufacture of a medicament for use in the treatment of acromegaly; gigantism; growth hormone deficiency, Turners syndrome; renal failure; osteoporosis, diabetes mellitus, cancer; obesity; insulin resistance; hyperlipidaemia; hypertension (leptin chimera); anaemia; autoimmune and infectious disease; inflammatory disorders including rheumatoid arthritis.

According to a further aspect of the invention there is provided a pharmaceutical composition comprising the binding agent according to the invention. Preferably said pharmaceutical composition includes a carrier, excipient and/or a diluent.

The invention also provides for a method of treating a human animal subject comprising administering an effective amount of the pharmaceutical composition/medicament to said subject.

It will be apparent to one skilled in the art that the compositions/medicaments can be provided in the form of an oral or nasal spray, an aerosol, suspension, emulsion, and/or eye drop fluid. Alternatively the medicament may be provided in tablet form. Alternative delivery means include inhalers or nebulisers.

Alternatively or preferably the medicament can be delivered by direct injection. It is also envisioned that the compositions/medicaments be delivered intravenously, intramuscularly, subcutaneously or topically. Further still, the compositions/medicaments may be taken orally or rectally.

The invention also provides a method of reduced renal clearance of a molecule comprising forming a binding agent according to any embodiment of the invention An embodiment of the invention will now be described by example only and with reference to the following figures wherein;

FIG. 2 represents the sequence (SEQ ID NO: 1) of the cDNA of the 588 bp PCR amplified GH fragment; (The 3'-Not1 site and two stop codons are shown in bold and italics respectively)

Figure 1A:
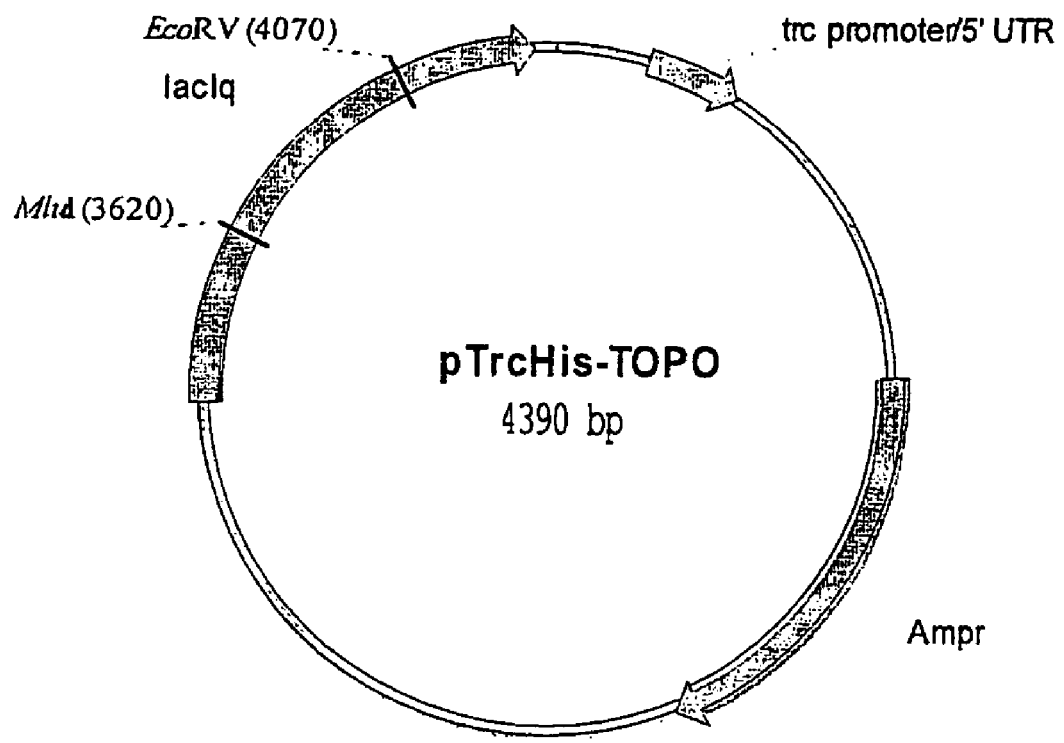
FIG. 1 represents a schematic diagram of (a) pTrcHis-TOPO and its derivatives; (b) pTrcHis-TOPO/GHstop;(c) pTrcHis-TOPO/Ghstop/GHR;(d)pTrcHis-TOPO/GH/link/GHR; (e) pTrcHis-TOPO/GH/link/flecGHRstop; f) pJONEXGHstop; pJONEXGHstoplink GHR.
Figure 1B:
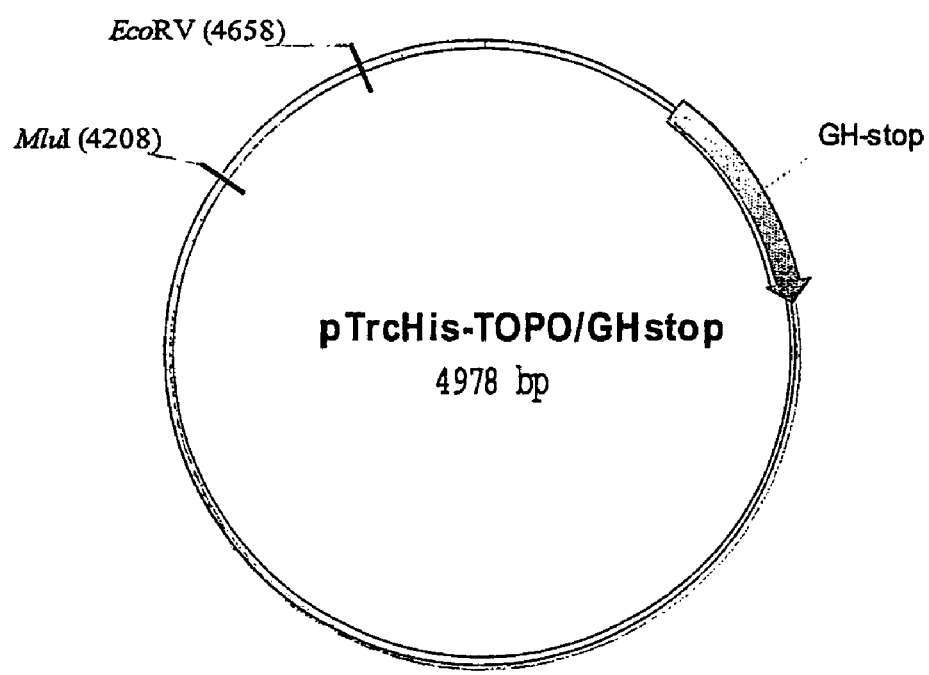
Figure 1C:
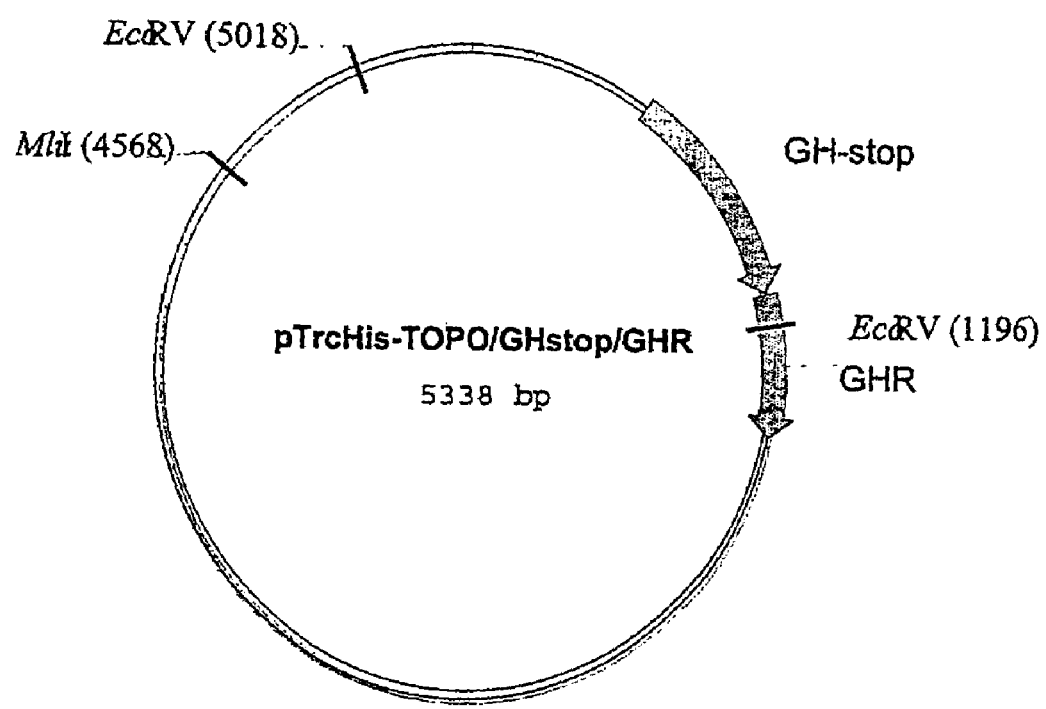
Figure 1D:
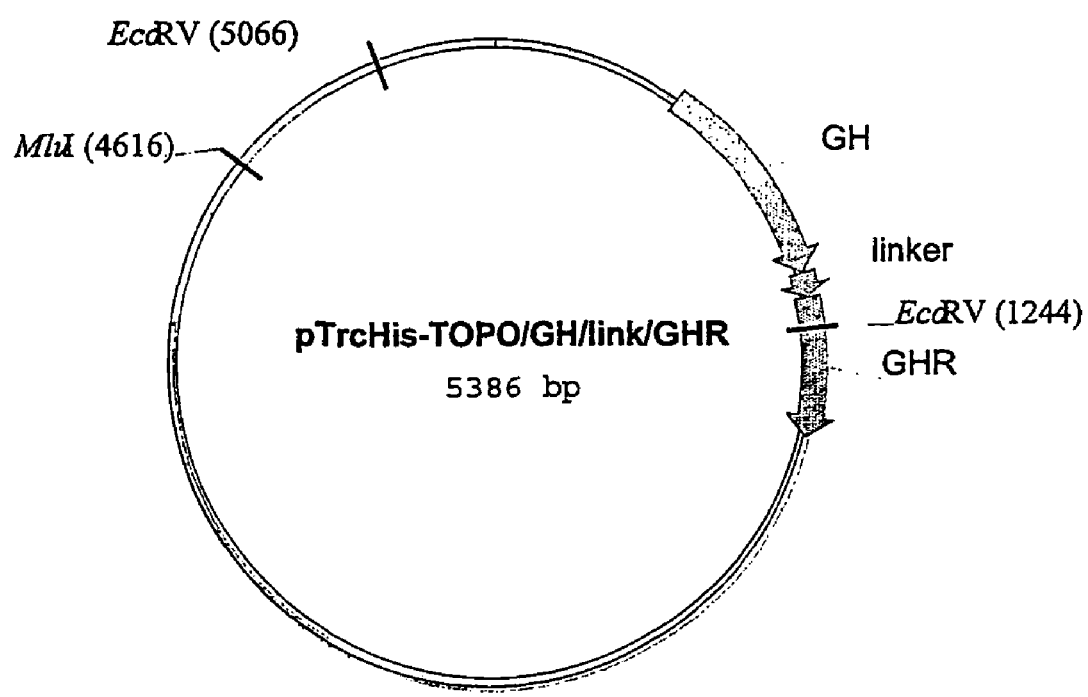
Figure 1E:
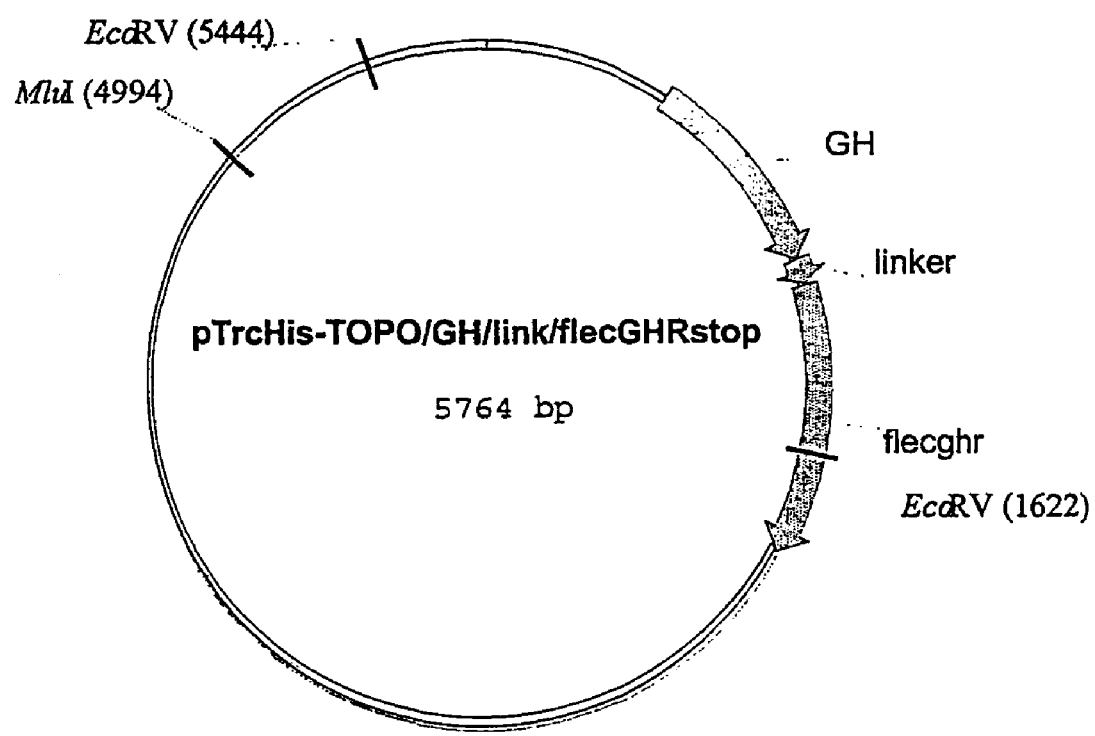
Figure 1F:
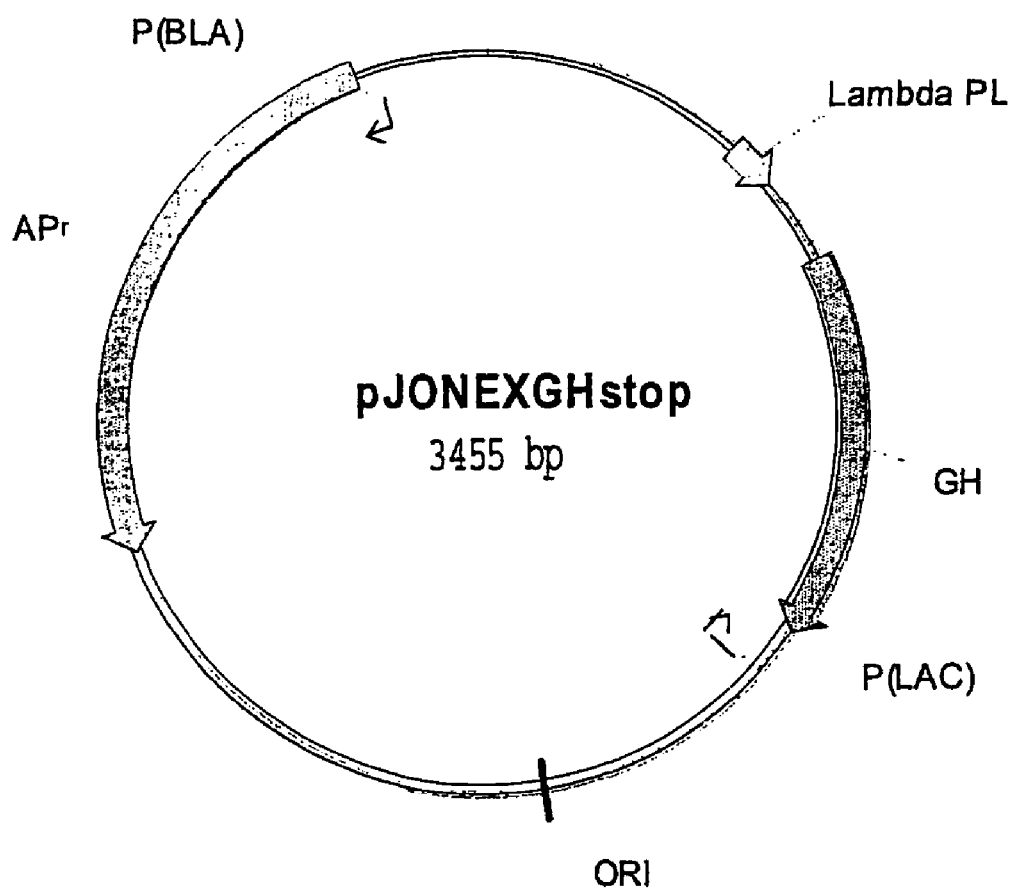
Figure 1G:
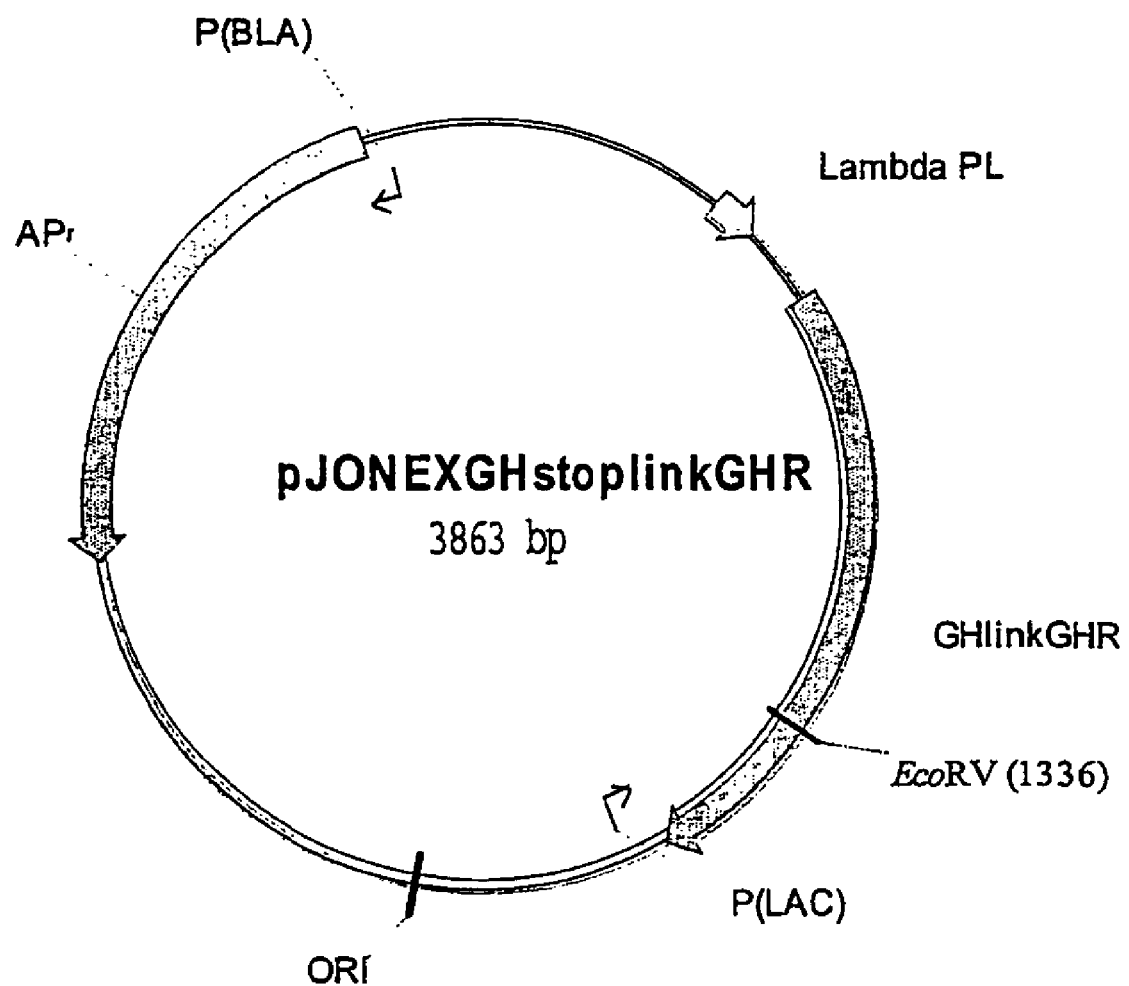
Figure 18:
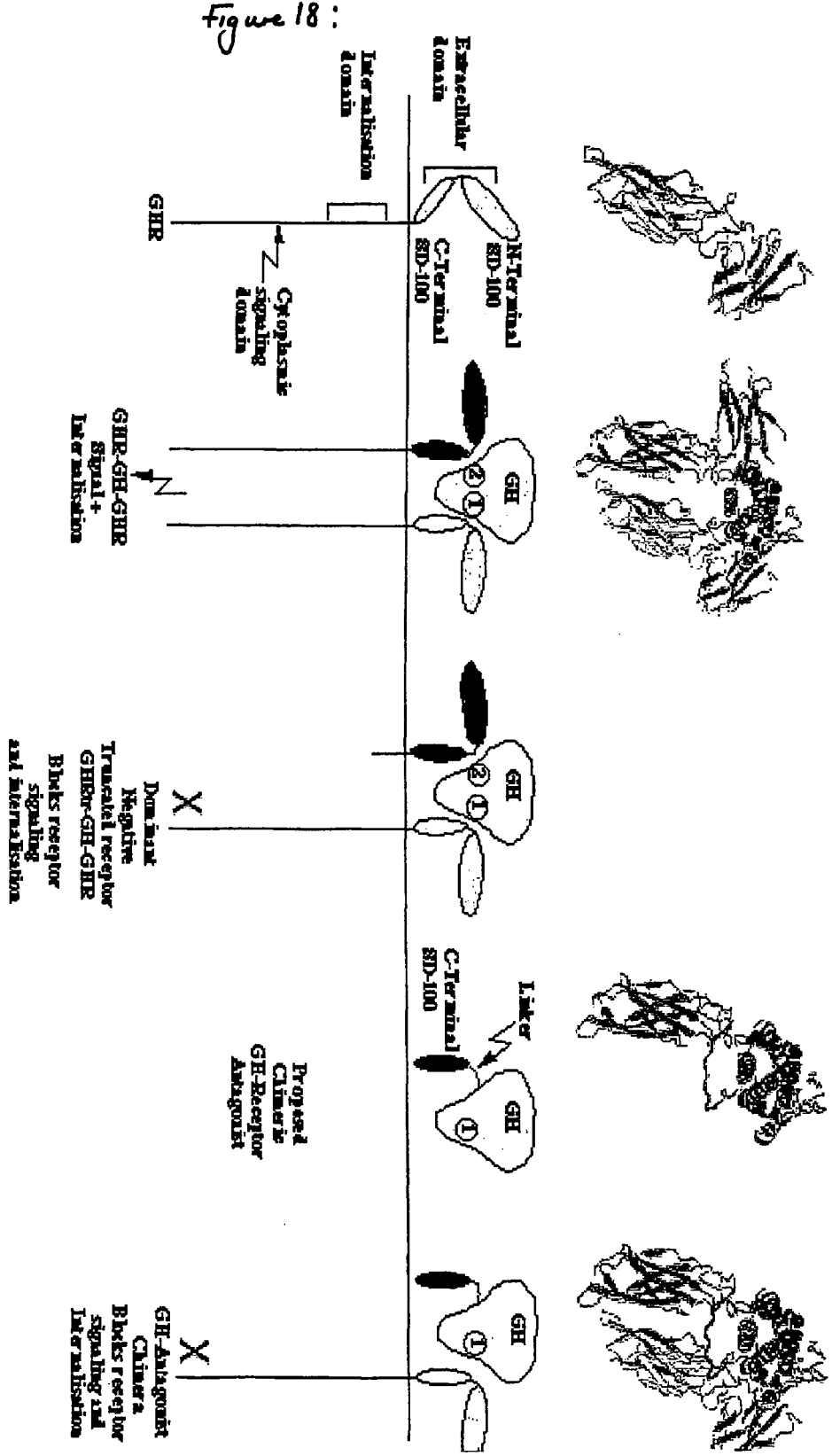

FIG. 3 represents the sequence (SEQ ID NO: 2) of the cDNA of the 390 bp PCR amplified GHR SD 100 fragment (The 5' EcoRI and 3' HindIII restriction sites are shown in bold and the 3' stop codons are shown in italics);

FIG. 4 represents the nucleic acid sequence (SEQ ID NO: 3) of the fill length GHstopGHR SD100 construct;

FIG. 5 represents the nucleic acid sequence (SEQ ID NO: 4) of the full length GHlinkGHR construct (Not1, EcoRI and HindIII restriction sites are shown in bold and the two 3' stop codons are shown in italics);

FIG. 6 represents the protein sequence (SEQ ID NO: 5) of full length GHlinkGHR (340 amino acids);

FIG. 7 represents the nucleic acid sequence (SEQ ID NO: 6) of the 762 bp PCR amplified full length extracellular domain of GHR (GHRflec) (the 5' EcoRI and HindIII sites are shown in bold and the two 3' stop codons are shown in italics);

FIG. 8 represents the full length nucleic acid sequence (SEQ ID NO: 7) of the GHlinkGHRflec construct (the Not1, EcoRI and HindIII site are shown in bold and the two 3' stop codons are shown in italics);

FIG. 9 represents the nucleic acid sequence (SEQ ID NO: 8) of the 1157 bp PCR fragment, GHlinkGHR generated by oligonucleotides TrcRBSsacF and GHRA835H, (the SacI, Not1, EcoRI and HindIII sites are shown in bold, the new ribosome binding site is shown in bold and underlined and the start/stop codons are shown in italics);

FIG. 10 represents the nucleic acid sequence (SEQ ID NO: 9) of the 740 bp PCR fragment, GHstop generated by nucleotides pTrcRBSsacI and TrcHindrev, (The SadI, Not1, EcoRI and HindIII sites are shown in bold, the new ribosome binding site is shown in bold and underlined and the start/stop codons are shown in italics);

FIG. 11 represents the amino acid sequence (SEQ ID NO: 10) of IL-6;

FIG. 12 represents the full length nucleic acid sequence (SEQ ID NO: 11) of gp130;

FIG. 13 represents the amino acid sequence (SEQ ID NO: 12) of the IL-6/gp130 fusion polypeptide;

FIG. 14 represents the nucleic acid sequence (SEQ ID NO: 13) of the gp 130 domain 1 deletion (616-2112 bp);

FIG. 15 represents the nucleic acid sequence (SEQ ID NO: 14) of gp130 domain 922-2112 bp;

FIG. 16 represents a western blot of induced proteins expressed by *E. coli* transformed with various vectors;

FIG. 17 (a) is a graphical representation of reporter gene assays for Ghstop and GH link GIR; and (b) quantification of the data represented in (a); and FIG. 18 is a schematic representation of GH:GHR interaction and GH:GHR chimera interaction with GHR.

FIG. 19 represents the in vitro agonist activity of the GH/GHR chimera.

FIG. 20 shows the results of a bioassay comparing the induction of a Stat5 reporter (luciferase activity) by growth hormone (GH), a negative control (XL blue) and partially purified antagonist (Chimera 1A2)

FIG. 21 represents the nucleotide sequence (SEQ ID NO: 15) of the Chi 1A2 chimera.

FIG. 22 represents the protein sequence (SEQ ID NO: 16) of Chi 1A2 chimera (311 amino acids).

MATERIALS AND METHODS

Table 3 explains the nomenclature used to define the protein constructs.

Generation of GH:GHR Fusion Protein

Six constructs are cloned (including 3 different lengths of linker with or without the C241 of the GHR) into a C-terminal poly-His expression vector. Human GH is amplified using high fidelity proof reading Pfu with convenient restriction sites to clone into the vector. The C-terminus SD-100 GHR is similarly amplified and the linker constructed in the primer with convenient restriction sites to clone into the C-terminus of GH. The constructs are then fully sequenced.

From the crystal structure of the GHR-GH-GHR complex, the distance between the C-terminus of GH (residue 191) and N-terminus of the C-Terminus SD-100 GHR (residue 126-128) is 10 A. Linkers between 10-20 residues are designed and three constructs made with linkers of either 10, 15 or 20 residues comprising of 2, 3 or 4 copies of the basic Gly$_4$Ser linker.

Protein Purification

The constructs are expressed in *E. coli* (JM109) and the protein purified on Invitrogen Xpress System Nickel columns with a secondary purification step by ion exchange chromatography. Lipopolysaccharide should not interfere with the bioassay as this requires a relatively short incubation in the cell culture system. If required the chimera antagonist is further purified using polymyxin B columns (Pierce).

Screening of Antagonist Activity

An established bioassay is used to screen for antagonist activity (9). A permanent cell line expressing the full length GHR is transiently transfected with a luciferase reporter that binds activated Stat5 (9). Twenty-four hours later the cells are stimulated with GH for 6 hours with or without antagonist. The cells are then lysed and luciferase activity measured (9).

Screening of Agonist Activity

A permanent cell line expressing the full length GHR is transiently transfected with a luciferase reporter that binds activated Stat5 (9). Twenty-four hours later the cells are stimulated with or without the GH/GBR chimera for 6 hours. The cells are then lysed and luciferase activity measured (9).

PCR OF Pituitary GH from Pituitary cDNA to Generate GHstop

Full-length human growth hormone was amplified from human pituitary cDNA using the Boehringer Expand High Fidelity PCR System. Each reaction consisted of: Primers GHS1-23 (forward) and GHA573not (reverse) 10 μM each, 200 μM dNTPs, 5 μl Expand buffer plus magnesium chloride (1.5 mM), and 0.6 μl High fidelity enzyme mix in a total volume of 50 μl.

Samples were as follows
1. Pituitary cDNA using GHS1-23 and GHA573 not primers
2. Pituitary cDNA using actin specific primers
3. Control cDNA for actin
4. Water control.

| PCR reaction master mix 1. | | | | |
|---|---|---|---|---|
| cDNA | 2 μl pituitary cDNA | 2 μl pituitary cDNA | 2 μl control cDNA | 2 μl water |
| Forward primer (10 μM stock) | 2 μl GHS1-23 | Actin primer 1 μl | Actin primer 1 μl | 2 μl GHS1-23 |
| Reverse primer (10 μM stock) | 2 μl GHA573not | Actin primer 1 μl | Actin primer 1 μl | 2 μl GHA573not |
| dNTP (10 mM stock) | 2 μl | 2 μl | 2 μl | 2 μl |
| Sterile water | 17 μl | 19 μl | 19 μl | 17 μl |

Master Mix 2 (per reaction)
10× Expand High Fidelity buffer (plus magnesium) (5 μl)
Sterile distilled water (19.4 μl)
Expand High Fidelity Expand polymerase (0.6 μl)
Added 25 μl Master Mix 2 to Master mix 1 and overlaid with oil.
PCR was carried out to the following method:
94° C.: 2 minutes,
94° C.: 30sec/54° C.: 1 minute/72° C.: 1 minute, for 30 cycles
72° C.: 10 min.

The 5'-nucleotide (GHS1-23) has sequence homology to the 5' end of the growth hormone gene and the 3'-nucleotide (GHA573not) contains a Not I site together with two stop codons. The PCR reaction produced a band of 588 bp (see FIG. 2) containing full-length human growth hormone. The fragment was then purified using the QIAquick PCR purification kit (Qiagen) and subsequently TOPO cloned into the pTrcHis-TOPO vector (Invitrogen, see FIG. 1). Ligations were transformed in to *E. coli* TOPO one shot cells (Invitrogen) by the calcium chloride method. Plasmid mini preparations were produced from positive transformants and screened by restriction digest using PstI/EcoRI. Clones with the correct insert size were then sequenced using vector specific primers supplied by invitrogen that bind 5' and 3' to the insert region (Xpress forward primer and pTrcHis reverse primer, see Table 1). This construct was named pTrcHisGHstop and was used as the template for subsequent cloning reactions.

Forward Primer for Growth Hormone Primer "GHS1-23":
5' ttcccaaccattcccttatccag 3' (SEQ ID NO: 18)
Reverse Primer GHA573not
5' ttatcagcggccgccgaagccacagctgccctccac 3' (SEQ ID NO: 19)

PCR of GHR C-Terminal SD100 Domain from Human Liver cDNA

The GHR C-terminal SD100 domain (FIG. 3) was amplified from human liver cDNA using the same PCR method as previously described, but using primers GHRS476 (forward) and GHRA835H (reverse), see table 1. The 5'-nucleotide contains an EcoRI site whilst the 3'-nucleotide contains two stop codons and a HindIII site.

The PCR reaction was carried out and cleaned up as described previously.
Samples were as follows:
1. liver cDNA using GHR476 and GHRA835H
2. liver cDNA using actin specific primers
3. Control cDNA
4. Water control.

| PCR reaction: Master Mix 1 | | | | |
|---|---|---|---|---|
| cDNA | 1 μl liver cDNA | 1 μl liver cDNA | 1 μl control cDNA | 1 μl Sterile water |
| Forward primer (10 μM stock) | 2 μl GHRS476 | Actin primer 1 μl | Actin primer 1 μl | 2 μl GHRS476 |
| Reverse primer (10 μM stock) | 2 μl GHRA835H | Actin primer 1 μl | Actin primer 1 μl | 2 μl GHRA835H |
| DNTP (10 mM stock) | 2 μl | 2 μl | 2 μl | 2 μl |
| Sterile Water | 18 μl | 19 μl | 19 μl | 17 μl |

Master Mix 2 (per reaction)
10× Expand High Fidelity buffer (plus MgC12) (5 μl)
Sterile distilled water (19.4 μl)
High Fidelity Expand polymerase (0.6 μl)
Added 25 μl Master Mix 2 to Master mix 1 and overlaid with oil.

Both vector, pTrcHisGHstop, and PCR product were subjected to a double digest using EcoRI and HinidIII restriction enzymes (Promega). The PCR product was cleaned up using QIAquick PCR purification kit and the digested pTrcHisGHstop vector was separated by agarose gel electrophoresis and purified using the QIAquick gel extraction kit The digested PCR fragment containing the C-terminal SD100 domain of GHR was then ligated to the above digested vector and transformed in to TOPO one shot cells (invitrogen) by the calcium chloride method. Ligations were transformed in to *E. coli* TOPO one shot cells (Invitrogen). Plasmid mini preparations were produced from positive transformants and screened by restriction digest using BamHI/EcoRI (Promega) and by PCR screening using GHS1-23 and GHRA835H primers. Clones with the correct insert size were then sequenced using pTrcHis reverse and GHseqF primers (see Table 1). This vector was called pTrcHisGHstopGHR and was used as the vehicle for the insertion of linker regions of varying lengths between GH and GHR in to the Not1/EcoRI sites. FIG. 4 shows the fill insert sequence for pTrcHisGHstopGHRP This construct allows the insertion of a linker molecule in to the Not1/EcoRI sites between Ghstop and GHlinkGHR.

Insertion of Linker Regions

The initial linker was constructed composed of a 4× repeating sequence of four glycine residues and one serine residue (20 residues in total) by annealing oligonucleotides G4S4 (forward) and G4COM4 (reverse) see Table 1. The 5'-nucleotide contains a NotI site and the 3'-nucleotide contains an EcoRI site. The vector pTrcHisGHstopGHR, was double digested with Not1 and HindIII restriction enzymes and cleaned up using the QIAquick clean up kit (Qiagen).

"G4S4"

5'ggccgcggtggcggaggtagtggtggcg-
 gaggtagcggtggcggaggttctggtggcggaggttccg 3' (SEQ ID NO: 20)

"G4COMS4"

5'aattcggaacctccgccaccagaacctc-
 cgccaccgctacctccgccaccactacctccgccaccgc 3' (SEQ ID NO: 21)

Preparation of Linker Insert:

Oligonucleotides G4S4 and G4COMS4 were resuspended in annealing buffer [10 mM Tris-HCl, pH 7.5, 50 mM NaCl, 1 mM EDTA] to a final concentration 0.1 pmol/μl. An equal volume of each oligonucleotide was then mixed and heated to 95° C. for 2 minutes and then allowed to cool over a 1 hour period.

The oligonucleotide duplexes were then ligated to the Not1/EcoRI double digested vector pTrcHisGHstopGHR and transformed in to TOPO one shot cells (Invitrogen) by the calcium chloride method. Plasmid mini preparations were produced from positive transformants and screened by restriction digest using Not1/EcoRI and by PCR screening using GHS 1-23 and GHRA835H primers. Clones with the correct insert size were then sequenced using pTrcHis reverse primer and GHseqF (see Table 1). This vector was called pTrcHisGHlinkGHR (See FIG. 1).

The ligation process removes the 3' stop codons within the GHstop region thus allowing transcription of the full length GHlinkGHR.

The same strategy was employed in order to clone in the full length extracellular domain of GHR incorporating SD 100 N and C-terminal domains.

Construction of Full Length Extracellular Domain of GUR (GHRflec)

The full length extracellular domain of GHR (SD100 N and C-terminal) was amplified using primers GHRS1ECOR and GHRA835H (see Table 1) following the same PCR protocol as described earlier for the generation of GHstop. The 5'-nucleotide (GERS1ECOR) contains an EcoRI site and the 3'-nucleotide contains a HindIII site. The PCR reaction produced a band of 762 bp (see FIG. 7) containing full length extracellular GHR and purified using Qiaquick PCR clean up kit (Qiagen). Both vector, pTrcHisGHlinkGHR and PCR product were subjected to a double restriction digest using EcoRI and HindIII restriction enzymes. The PCR product was cleaned up using QIAquick PCR clean up kits and the digested vector was separated by agarose gel electrophoresis and subsequently purified using the QIAquick gel extraction kit.

Both vector, pTrcHisGHlinkGHR, and PCR product were double digested with EcoRI and HindIII, and cleaned up using QIAquick clean up kits (Qiagen). The digested PCR fragment was then ligated in to the digested pTrcHis-GHlinkGHR vector and transformed in to TOPO one shot cells (Invitrogen) by the calcium chloride method. Positive transformants were screened by restriction digest using EcoRI and HindIII and by PCR using primers GHRS1ECOR and GHRA835H. Clones with the correct sized insert were sequenced using GHseqF and the vector specific primer pTrcHis reverse. The new construct was called pTrcHis-GHlinkGHRflec. This can then be used as a template for any future linker inserts.

Cloning GHstop and GHlinkGHR into pJONEX4 pJONEX4 vector (See FIG. 1) was constructed in order to express inducible proteins that were potentially deleterious to the cell by placing them under the control of a strong repressor of transcription (cI857) and a heat inducible promoter (PLλ). The construction of pJONEX4 has been described elsewhere (Jon R. Sayers and Fritz Eckstein; Nucleic Acid Research, volume19, No15, p4127-4132, 1991).

The PLλ promoter region was cloned into pUC19 in the EcoRI site and engineered so that only one EcoRI site remained downstream of the promoter to produce pJONEX4. Genes wishing to be transcribed can be inserted into the SacI/HindIII region downstream of the PLλ promoter. This vector can be used to transform bacteria which specify a temperature sensitive lambda repressor (cI857), thus at low temperatures, below 30° C., transcription read through is prevented by the presence of the repressor protein. However, at higher temperatures (42° C.) induction of protein expression proceeds. The main aim was to construct primers in order to PCR up the fill length GHstop and GHlinkGHR from their parent vector pTrcHis-TOPO and subclone these fragments into the SacI/HindIII sites in pJONEX4.

5'-nucleotide, TrcRBSsacF contains an engineered SacI restriction site, a new ribosome binding site and the ATG start codon present in the pTrcHis-TOPO vector. Two 3'-nucleotides will be used to PCR GHstop and GHlinkGHR respectively from their parent vectors, pTrcHis. The 3'-nucleotide, TrcHindrev, contains a HindIII site and will be used to PCR the full length GHstop gene. The other nucleotide, GHRA835H has already been described, and will be used to PCR up GHlinkGHR (see Table 1).

TrcRBSSacIf:

```
5' gggaaa gagctc aaggagaaaataaa atg
         SacI        RBS      START
ggggggttctcatcatcat 3' (SEQ ID NO: 22)
   pTrc vector
```

TrcHindIIIrev:

5'gccaagcttcgaattgaattcg 3' (SEQ ID NO: 23)

PCR Method

96° C. 2 mins

94° C. 30 sec/54° C. 1 min, for 30 cycles

72° C. 10 mins

| PCR reaction; Master Mix 1 | | | | |
|---|---|---|---|---|
| Plasmid (100 ng total) | 2 μl pTrcHisGHstop | 2 μl pTrcHisGhlinkGHR | 2 μl water | 2 μl water |
| Forward primer (10 mM stock) | 2 μl TrcRBSsac1 | 2 μl TrcRBSsac1 | 2 μl TrcRBSsac1 | 2 μl TrcRBSsac1 |
| Reverse primer (10 mM stock) | 2 μl TrcHindrev | 2 μl GHRA835H | 2 μl TrcHindrev | 2 μl GHRA835H |
| DNTP (10 mM stock) | 2 μl | 2 μl | 2 μl | 2 μl |
| Sterile water | 17 μl | 17 μl | 17 μl | 17 μl |
| Total volume | 25 μl | 25 μl | 25 μl | 25 μl |

15

Master Mix 2 (Per Reaction)
Expand High Fidelity buffer (plus magnesium, 1.5 mM final) (5 μl)
Expand High Fidelity polymerase: (0.6 μl)
Sterile water: (19.4 μl)
Added 25 μl Master Mix 2 to Master mix 1 and overlaid with mineral oil.

Both PCR fragments and pJONEX4 vector were subjected to a double restriction digest using SacI/HindIII and purified using the QLAquick clean up kits (Qiagen). The digested PCR fragment was then ligated to the above digested vector and transformed in to *E. coli* M72 (λ) cells by the method of electroporation. Plasmid mini preps were produced from positive transformants and screened by restriction digest using Sac/HindIII and by PCR using nucleotides TrcRBSsac1 and TrcHindrev for Ghstop and TrcRBSsac1 and GHRA835H for GHlinkGHR Clones with the correct insert size were then sequenced using GHS1-23, GhseqF, Xpress forward and GHA573not.

Cloning Full Length IL-6 and gp130 into pTZ18U/pTrcHis-TOPO/pJONEX4 Vectors

The IL-6/gp130 chimeras are provided in a variety of vectors. Cloning into pTZ18U will facilitate in vitro mutagenisis and the pJONEX and pTrcHis-TOPO vectors can be used to generate recombinant protein in *E. coli* which can be purified using Nickel columns.

Cloning is into pTrcHis using the TA cloning strategy devised for Ghstop/GHlinkGHR. The chimeras are then subcloned into the pJonex and pTZ18U system using the restriction sites BarH1/HindIII. This would maintain the upstream RBS and Hist6 tag in pJONEX and allow insertion into pTZ18U (they have the same multiple cloning site) for mutagenesis experiments.

The strategy is to TA clone in IL-6 (fill length: see sequence below: FIG. 1) with the 3'prime nucleotide containing a Not 1 site together with another restriction site: Sal1 (or Xho1). This Sal1 site will thus allow the cloning of the gp130 gene in to the Sal1/HindIII sites (HindIII being in 3 'end of the pTrcHis vector). The linker can then be inserted into the Not1/Sal1 sites.

The construct once sequenced is subcloned into the pJonex and pTZ18U vectors using BamHI/HindIII.

IL-6 and gp130 are amplified by PCR from IMAGE clones or cDNA from human lymphocytes.

The following primers will be used in TA cloning of the IL-6 sequence as represented in FIG. 11 into pTrcHis.

Primers for Cloning IL-6 into pTrcHis
Forward (5'nucleotide) PRIMER 1
5' gtaccccagg agaagattcc aaagatgtag 3' (31 mer with 15 gc) (SEQ ID NO: 24)

Reverse Primer (3'nucleotide: NotI/SalI and Stop codons are shown in bold, sequence shown in italics and underlined is insert sequence to keep sequence in frame and as an overhang for NotI/SalI digestion and incorporates the stop codons)
Primer 2
5' tgagggctcttcggcaaatg g gcggccgc tgataa gtcgac 3' (20 mer with 11 gc) (SEQ ID NO: 25)
5' cagctg aatagt cgccggcg g gtaaacggcttctcgggagt 3' (SEQ ID NO: 26)
5' gtcgac ttatca gcggccgc c catttgccgaagagccctca 3' (reverse nucleotide) (SEQ ID NO: 27)

The next stage is to sub-clone the gp130 full length extracellular domain (322-2112 bp; see FIG. 12). Clone gp130 into the Sal1/HindIII sites Primers for Cloning Full Length gp130 into pTrcHis-TOPO
Forward primer (5' nucleotide: SalI site shown in bold)
PRIMER 3
5' gggaaa gtcgac gaacttcta gatccatgtg gtt3' (22 mer 9 gc) (SEQ ID NO: 28)
Reverse primer (HindIII and stop codons shown in bold)
PRIMER 4
5' ccaaa gtttgct caaggagaaaattgaa tgataa aagctt gggaaa 3' (SEQ ID NO: 29)
5' aaaggg ttcgaa aatagt aagttaaagaggaac tcgttg aaacc3' (SEQ ID NO: 30)
5' tttccc aagctt ttatca ttcaatttctccttg agcaaac tttgg3' (reverse nucleotide) (SEQ ID NO: 31)

The step 3 is to ligate in the linker duplex that contain a 5'Not1 site and a 3'Sal1 site.

Linker Duplex
G4S4 Not/SalI (5' overhang for Not1 and 3' overhang for SalI are in bold) PRIMER 7
5'  ggccgcggtggcggaggtagtggtggcg-gaggtagcggtggcggaggttctggtggcggaggttcc g (SEQ ID NO: 32)
G4S4rev/Not/Sal 1(5' overhang for Not1 and SalI are shown in bold) PRIMER 8
5'  tcgac gaacctccgccaccagaacctccgccac-cgctacctccgccaccactacctccgccacc gc 3' (SEQ ID NO: 33)

This produces a full length construct: JL-6/link/gp130. The next step is to carry out cloning of domain deletions of gp130 into the SalI/HindIII sites.

Primers for Cloning gp130 D1 Deletion in to pTrcHis-TOPO (SalI/HindIII Sites)
forward primer (SalI site shown in bold) PRIMER 5
5' gggaaa gtcgac atttcaggcttgcctcca 3' (SEQ ID NO: 34)
Reverse primer (HindIII and stop condons shown in bold)
PRIMER 4
5' ccaaa gtttgct caaggagaaaattgaa tgataa aagctt gggaaa 3' (SEQ ID NO: 29)

5' aaaggg ttcgaa aatagt aagttaaagaggacc tcgtttg aaacc 3' (SEQ ID NO: 30)

5' ttttccc aagctt ttatca ttcaatttctccttg agcaaac tttgg 3' (reverse nucleotide) (SEQ ID NO: 31)

The next step is to clone in gp130 truncation up to 922 bp (this deletes domains 1 and 2 from the extracellular region of gp130). Construct IL-6/link/gp130D1

Primer for Cloning gp130 (922-2112bp Fragment)
Forward primer (SalI site shown in bold) PRIMER 6
5' gggaaa gtcgac aatccgccacaataatttat 3' (SEQ ID NO: 35)
Reverse primer (HindIII and stop condons shown in bold) PRIMER 4
5' ccaaa gtttgct caaggagaaattgaa tgataa aagctt gggaaa 3' (SEQ ID NO: 29)
5' aaaggg ttcgaa aatagt aagttaaagaggaac tcgtttg aaacc 3' (SEQ ID NO: 30)
5' ttttccc aagctt ttatca ttcaatttctccttg agcaaac tttgg 3' (SEQ ID NO: 31)

Preparation of Electrocompetant M72 (λ) Cells

M72 (λ) cells were grown o/n in 50 ml LB. 100 ml of this o/n culture was then added to 900 ml LB and grown at 30° C. until OD600 was between 0.5-0.6. Cells were then harvested at 4000 rpm, 20 min at room temperature using a Sorval RC-3B centrifuge. The pellet was resuspended and re-centrifuged at 4000 rpm, 4° C., 20 minutes in gradually reducing volumes of sterile ice cold 10% (v/v) glycerol of 1000 ml, 500 ml, 250 ml. The pellet was finally resuspended in 1000 µl of 10% (v/v) glycerol, divided in to 100 µL aliquots, flash frozen in liquid nitrogen and stored at −80° C.

Transformation of M72 Cells.

Electrocompetant M72 (λ) cells were defrosted on ice and placed in to an electroporation cuvette (cell width of 0.1 cm, Invitrogen) and electroporated at 1.8 KV. Positive transformants were selected for on LB plates supplemented with 100 µg/ml ampicillin and grown at 30° C. overnight.

Induction of Expression of Constructs from pTrcHis-TOPO Vectors

Transformed *E. coli* TOP 10 cells were grown overnight at 37° C. with shaking at 200 rpm in 10 ml LB supplemented with ampicillin (100 µg/ml final). The next day 5 ml of the overnight was used to seed 250 ml LB supplemented with ampicillin (100 µg/ml final) and grown to an OD600=0.6. The culture was then induced with the addition of IPTG to a final concentration of 1 mM and the cells grown for a further 5 hrs. Induced cells were then harvested by centrifugation at 13000 rpm, room temperature and the pellet either frozen or lysed.

Induction of Expression of Constructs from pJONEX Vectors

Transformed *E. coli* M72 (λ) cells were grown o/n at 30° C. with shaking at 2000 rpm in LB supplemented with ampicillin (100 µg/ml). The next day the o/n culture was used to seed fresh LB and cells were grown until an OD600 of approximately 0.6 was reached. The temperature of the incubator was then adjusted to 42° C. and an equal volume of pre-warned media was added to bring the temperature of the culture up to 42° C. The cells were then grown at 42° C. for a further 4-5 hrs then harvested.

Purification of Induced Proteins by Immobilised Metal Affinity Chromatography (IMAC)

Induced cell pellets were resuspended in 20 mM sodium phosphate buffer, 500 mM sodium chloride, pH 7.8 and lysed by the addition of hen egg white lysozyme to a final concentration of 100 µg/ml, and left on ice for 15 minutes. The cells suspension was then sonicated by applying three 10 second bursts on a medium intensity setting whilst holding on ice. Insoluble material was then removed by centrifugation at 40000×g, 4° C. for 20 minutes in a RC-3B centrifuge.

The cleared cell lysate was then applied to a Probond resin column (Invitrogen) pre-equilibrated with 20 mM sodium phosphate buffer, 500 mM NaCl, pH 7.8. The column washed with 20 mM sodium phosphate buffer, 500 mM sodium chloride, pH 7.8 buffer followed by washing with 20 mM sodium phosphate buffer, 500 mM sodium chloride, pH 6.0. Bound protein was eluted by an increasing gradient of 50 mM to 500 mM imidazole made up in 20 mM sodium phosphate buffer, 500 nM sodium chloride, pH 6.0 buffer. 1 ml fractions were collected and purification monitored by bradford protein assay and SDS-PAGE. Fractions containing proteins of interest were pooled and dialysed against 1000 volumes 20 mM sodium phosphate buffer, pH 7.8, for 2, 4 and 6 hours respectively. Dialysed protein was then concentrated (if needed) using an Amicon Centriprep Y-10 column. Dialysed and concentrated samples were then either stored at 4° C. or frozen or used directly in a bioassay for growth hormone activity.

Bioassay of rGH and Purified Growth Hormone Constructs

Hek293 cells were previously stably transfected with full-length human growth hormone receptor. Cells were routinely cultured in Dulbeccos MEM/Nutrient F12 medium supplemented with 10% Foetal calf serum, 1% penicillin/streptomycin and 1% L-glutamine. Cells used for the bioassay were first dissociated, counted, then plated at 2×105 cells/ml in growth medium in a 12 well plate and grown o/n at 37° C., 5% CO2. The next day cells were placed in rich medium [⅔ Dulbeccos MEM/12 nutrient medium, ⅓ Dulbeccos 4.5 g/L-glucose, 10% Foetal calf serum, 1% penecillin/streptomycin and 1% L-glutamine] and incubated for 6 hours at 37° C. Transfection with reporter gene constructs was completed using the calcium phosphate transfection system (Life Technologies) according to the manufactures instructions. Cells were left overnight at 37° C., 5% $CO_2$. The next day cells were challenged with recombinant protein from 5-5000 ng/ml, made up in starvation medium [⅔Dulbeccos MEM/Nutrient F12 medium supplemented with 1% penicillin/streptomycin, 1% L-glutamine] supplemented with 100 ng/µl dexamethasone. Where necessary recombinant wild type GH was mixed with purified GHstop or Chimeric protein in a competition assay. Cells were incubated at 37° C., 5% CO2 for at least 5 hours before assaying for luciferase and β-galactosidase activity.

Luciferase/β-Galactosidase Assay

The assays were performed according to the manufacturers instructions. Briefly media was aspirated from a 12 well plate and cells lysed with 150 µl reporter lysis buffer for 20 minutes at room temperature.

For the β-galactosidase assay 25 µl of each lysate was added to duplicate wells of a 96 well plate and mixed with 75 µl assay buffer. The plate was incubated at 37° C. until a yellow coloration had developed at which point the plate was read at 420 nm. For the luciferase assay, 50 µl of the remaining lysate was added to a luminometer cuvette to which was then added 50 µl of luciferase substrate. The sample was mixed by vortexing for 10 seconds and fluorescence measured at 15 and 60 second intervals.

The final data was corrected for β-galactosidase expression by presenting results as a ratio of luciferase:β-galactosidase activity measured. FIG. 17 shows data generated from a reporter gene assay using purified GH stop and GHlinkGHR.

Western Blotting

Samples from purification's were routinely analysed for growth hormone expression by first separating samples by 12% (v/v) SDS-PAGE under either reducing or non-reducing conditions and transferring to PVDF membrane. The membrane was then blocked in 4% (w/v) milk protein in PBS, supplemented with 0.05% (v/v) Tween 20 (PBS-T). The membrane was then probed with anti-growth hormone (10A7, mouse IgG1) at 1/2000 dilution in 1% (w/v) milk protein in PBS-T. After brief washing the membrane was probed with Sheep anti mouse-HRP (Amersham) at 1/5000 dilution in 1% (w/v) milk protein in PBS-T. After extensive washing with PBS-T, specific protein bands were visualised using ECL western blot detection reagents (Amersham). FIG. 16 shows a western blot of induced proteins expressed either in the pTrcHis-TOPO of pJONEX vector systems.

Radioimmunoassay for Growth Hormone

The human growth hormone assay was performed using the NETRIA human growth hormone IRMA assay which uses a rabbit polyclonal and a labelled monoclonal antibody.

TABLE 1

RIA results for induced lysates of Ghstop and GHlinkGHR

| Sample | Value (m U/L) |
| --- | --- |
| Ghstop induced cell lysate | 583 |
| GHlinkGHR induced cell lysate | 504 |
| Non-transfected cell lysate | 42 |

Testing Metabolic Clearance Rate In Vivo

Sprague-Dawley rats are anaesthetised and cannulae implanted in femoral and jugular veins. Two days later GH or chimera is administered by intravenous or subcutaneous injection. Blood samples are collected via the femoral cannula and chimera levels measured by radio-immunoassay (see table 2). Pharmacokinetic parameters are estimated using available computer programs fitting hormone concentration against time.

Activation of GH Signalling, Measured as Luciferase Activity, by GH, Negative Control Purification and Chi 1A2 (GiH Fused to GHR)

A number of chimeric constructs were made. The partially purified chimera was prepared from transformed XL blue *E. coli*. Protein from untransformed XL blue *E. coli* was purified over nickel columns and used as a negative control to detect any non-specific agonist or antagonist action. All purified proteins were stored in glycerol.

The negative control and Chimera IA2 were incubated with and without GH.

FIG. 19 shows results of bioassay comparing the induction of a Stat5 reporter (luciferase activity) by growth hormone (GH), negative control (E blue), and partially purified antagonist (Chimera 1A2).

The graph shows the expected dose-response to GH. Incubation with negative control showed no induction of luciferase activity but at high concentration partially inhibited the bioassay (this may be an effect of the increased glycerol concentration). At 500 ng/ml Chimera 1 A2 appeared to completely block GH signalling.

REFERENCES

1. Kishimoto, T., T. Taga, and S. Akira. 1994. Cytokine signal transduction. [Review] [92 refs]. *Cell* 76:253-262.
2. Muller-Newen, G., C. Kohne, and P. C. Heinrich. 1996. Soluble receptors for cytokines and growth factors. [Review] [58 refs]. *International Archives of Allergy & Immunology* 111:99-106.
3. Cunningham, B. C., M. Ultsch, A. M. de Vos, M. G. Mulkerrin, K. R. Clauser, and J. A. Wells. 1991. Dimerization of the extracellular domain of the human growth hormone receptor by a single hormone molecule. *Science* 254:821-825.
4. de Vos, A. M., M. Ultsch, and A. A. Kossiakoff. 1992. Human growth hormone and extracellular domain of its receptor: crystal structure of the complex. *Science* 255:306-312.
5. Sundstrom, M., T. Lundqvist, J. Rodin, L. B. Giebel, D. Milligan, and G. Norstedt. 1996. Crystal structure of an antagonist mutant of human growth hormone, G120R, in complex with its receptor at 2.9 A resolution. *Journal of Biological Chemistry* 271:32197-32203.
6. Clackson, T., M. H. Ultsch, J. A. Wells, and A. M. de Vos. 1998. Structural and functional analysis of the 1:1 growth hormone:receptor complex reveals the molecular basis for receptor affinity. *Journal of Molecular Biology* 277:1111-1128.
7. Argetsinger, L. S. and C. Carter-Su. 1996. Growth hormone signalling mechanisms: involvement of the tyrosine Idnase JAK2. [Review] [19 refs]. *Hormone Research* 45 Suppl 1:22-24.
8. Fuh, G., B. C. Cunningham, R. Fukunaga, S. Nagata, D. V. Goeddel, and J. A. Wells. 1992. Rational design of potent antagonists to the human growth hormone receptor. *Science* 256:1677-1680.
9. Ross, R. J., N. Esposito, X. Y. Shen, S. Von Laue, S. L. Chew, P. R. Dobson, M. C. Postel-Vinay, and J. Finidori. 1997. A short isoform of the human growth hormone receptor functions as a dominant negative inhibitor of the full-length receptor and generates large amounts of binding protein. *Molecular Endocrinology* 11:265-273.
10. Chen, C., R. Brinkworth, and M. J. Waters. 1997. The role of receptor dimerization domain residues in growth hormone signalling. *Journal of Biological Chemistry* 272:5133-5140.
11. Chen, W. Y., D. C. Wight, T. E. Wagner, and J. J. Kopchick. 1990. Expression of a mutated bovine growth hormone gene suppresses growth of transgenic mice. *Proceedings of the National Academy of Sciences of the United States of America* 87:5061-5065.
12. Chen, W. Y., D. C. Wight, B. V. Mehta, T. E. Wagner, and J. J. Kopehick. 1991. Glycine 119 of bovine growth hormone is critical for growth-promoting activity. *Molecular Endocrinology* 5:1845-1852.
13. Chen, W. Y., M. E. White, T. E. Wagner, and J. J. Kopchick. 1991. Functional antagonism between endogenous mouse growth hormone (GH) and a GH analog results in dwarf transgenic mice. *Endocrinology* 129:1402-1408.
14. Chen, W. Y., N. Y. Chen, J. Yun, T. E. Wagner, and J. J. Kopchick. 1994. In vitro and in vivo studies of antagonistic effects of human growth hormone analogs [published erratum appears in J Biol Chem 1994 Aug. 12; 269(32):20806]. *Journal of Biological Chemistry* 269:15892-15897.
15. Mellado, M., J. M. Rodriguez-Frade, L. Kremer, C. von Kobbe, A. M. de Ana, I. Merida, and A. Martinez. 1997. Conformational changes required in the human growth hormone receptor for growth hormone signalling. *Journal of Biological Chemistry* 272:9189-9196.
16. Maamra, M., J. Finidori, S. Von Laue, S. Simon, S. Justice, J. Webster, Dower, and R. Ross. 1999. Studies with a growth hormone antagonist and dual-fluorescent confocal microscopy demonstrate that the full-length human growth hormone receptor, but not the truncated isoform, is very rapidly internalized independent of Jak2-Stat5 signalling. *Journal of Biological Chemistry* 274:14791-14798.

17. Cunningham, B. C., H. B. Lowman, J. A. Wells, R. G. Clark, K. Olson, and G. Fuh. 1998. Human growth hormone variants. U.S. Pat. No. 5,849,535

18. Thorner, M. O., C. J. Strasburger, Z. Wu, M. Straume, M. Bidlingmaier, S. Pezzoli, K. Zib, J. C. Scarlett, and W. F. Bennett. 1999. Growth hormone (GH) receptor blockade with a PEG-modified GH (B2036-PEG) lowers serum insulin-like growth factor-I but does not acutely stimulate serum GH. *Journal of Clinical Endocrinology & Metabolism* 84:2098-2103.

19. Ayling, R. M., R. Ross, P. Towner, S. Von Laue, J. Finidori, S. Moutoussamy, C. R. Buchanan, P. E. Clayton, and M. R. Norman. 1997. A dominant-negative mutation of the growth hormone receptor causes familial short stature [letter]. *Nature Genetics* 16:13-14.

20. Quinton, N. D., R. F. Smith, P. E. Clayton, M. S. Gill, S. Shalet, S. K. Justice, Simon, S A, S. Walters, M. C. Postel-Vinay, A. I. F. Blakemore, Ross, and RJM. 1999. Leptin binding activity changes with age: The link between leptin and puberty. *Journal of Clinical Endocrinology & Metabolism* 84:2336-2341.

21. Haffner, D., F. Schaefer, J. Girard, E. Ritz, and O. Mehls. 1994. Metabolic clearance of recombinant human growth hormone in health and chronic renal failure. *Journal of Clinical Investigation* 93:1163-1171.

22. Maini, R., E. W. St Clair, F. Breedveld, D. Furst, J. Kalden, M. Weisman, Smolen, P. Emery, G. Harriman, M. Feldmann, and P. Lipsky. 1999. Infliximab (chimeric anti-tumour necrosis factor alpha monoclonal antibody) versus placebo in rheumatoid arthritis patients receiving concomitant methotrexate: a randomised phase HI trial. ATTRACT Study Group. *Lancet* 354:1932-1939.

23. Weinblatt, M. E., J. M. Kremer, A. D. Bankhurst, K. J. Bulpitt, R. M. Fleischmann, Fox, R I, C. G. Jackson, M. Lange, and D. J. Burge. 1999. A trial of etanercept, a recombinant tumor necrosis factor receptor:Fc fusion protein, in patients with rheumatoid arthritis receiving methotrexate [see comments]. *New England Journal of Medicine* 340:253-259.

24. Mohler, K. M., P. R. Sleath, J. N. Fitzner, D. P. Cerretti, M. Alderson, S. S. Kerwar, D. S. Torrance, C. Otten-Evans, T. Greenstreet, and K. Weerawarna. 1994. Protection against a lethal dose of endotoxin by an inhibitor of tumour necrosis factor processing. *Nature* 370:218-220.

25. Mohler, K. M., D. S. Torrance, C. A. Smith, R. G. Goodwin, K. E. Streinler, V. P. Fung, H. Madani, and M. B. Widmer. 1993. Soluble tumor necrosis factor (TNF) receptors are effective therapeutic agents in lethal endotoxernia and function simultaneously as both TNF carriers and TNF antagonists. *Journal of Immunology* 151:1548-1561.

26. Ghilardi, N., S. Ziegler, A. Wiesttner, R. Stoffel, M. H. Heim, and R. C. Skoda. 1996. Defective STAT signalling by the leptin receptor in diabetic mice. *Proceedings of the National Academy of Sciences of the United States of America* 93:6231-6235.

27. Tartaglia, L. A. 1997. The leptin receptor. [Review] [59 refs]. *Journal of Biological Chemistry* 272:6093-6096.

28. Tartaglia L A, Dembski M, Weng X et al. Identification and expression cloning of a leptin receptor, OB-R. Cell 1995; 83(7):1263-1271.

29. Livnah O, Stura E A, Middleton S A, Johnson D L, Jolliffe L K, Wilson I A. Crystallographic evidence for preformed dimers of erythropoietin receptor before ligand activation. Science 1999; 283(5404):987-990.

30. Remy I, Wilson I A, Michnick S W. Erythropoietin receptor activation by a ligand-induced conformation change. Science 1999; 283(5404):990-993.

31. BAUMANN, G. (1991) Growth hormone heterogeneity: genes, isohormones, variants, and binding proteins. *Endocrine Reviews,* 12, 424-449.

32. HAFFNER, D., SCHAEFER, F., GIRARD, J., RITZ, E. & MEHLS, O. (1994) Metabolic clearance of recombinant human growth hormone in health and chronic renal failure. *Journal of Clinical Investigation,* 93, 1163-1171.

33. JOHNSON, V. & MAACK, T. (1977) Renal extraction, filtration, absorption, and catabolism of growth hormone. *American Journal of Physiology,* 233, F185-F196

34. MANTZOROS, C. S. & FLIER, J. S. (2000) Editorial: leptin as a therapeutic agent—trials and tribulations. *Journal of Clinical Endocrinology & Metabolism,* 85, 4000-4002.

35. PEEL, C. J., BAUMAN, D. E., GOREWIT, R. C. & SNIFFEN, C. J. (1981) Effect of exogenous growth hormone on lactational performance in high yielding dairy cows. *Journal of Nutrition,* 111, 1662-1671.

36. SYED, S., SCHUYLER, P. D., KULCZYCKY, M. & SHEFFIELD, W. P. (1997) Potent antithrombin activity and delayed clearance from the circulation characterize recombinant hirudin genetically fused to albumin. *Blood,* 89, 3243-3252.

The invention claimed is:

1. A binding agent which is a fusion protein comprising the amino acid sequence set forth in SEQ ID NO: 5, wherein said binding agent is an agonist of a growth hormone receptor.

2. An isolated nucleic acid molecule comprising a nucleic acid sequence which encodes a binding agent according to claim 1.

3. An isolated nucleic acid molecule according to claim 2, comprising a nucleic acid sequence of SEQ ID NO: 4.

4. A vector comprising a nucleic acid molecule of claim 3.

5. A vector according to claim 4 wherein the vector is an expression vector.

6. A vector according to claim 5 wherein said vector is an expression vector adapted for prokaryotic gene expression.

7. A vector according to claim 5 wherein said vector is an expression vector adapted for eukaryotic gene expression.

8. A vector according to claim 5 wherein said vector further comprises a nucleotide sequence encoding a secretion signal to facilitate purification of a polypeptide expressed from the vector.

9. An isolated cell comprising a nucleic acid according to claim 2.

10. An isolated cell according to claim 9, wherein the cell is a eukaryotic cell.

11. An isolated cell according to claim 10, wherein said cell is selected from the group consisting of: fungal cell; insect cell; amphibian cell; plant cell and mammalian cell.

12. An isolated cell according to claim 9, wherein said cell is a prokaryotic cell.

13. An isolated cell according to claim 12 wherein said cell is *Escherichia coli*.

14. A composition comprising a binding agent according to claim 1, and a pharmaceutically acceptable carrier, excipient or diluent.

15. A method for treating growth hormone deficiency, the method comprising administering to a patient in need thereof a composition of claim 14.

16. A method for preparing a binding agent of claim 1, the method comprising:

i) growing an isolated cell comprising a nucleic acid molecule comprising a nucleic acid sequence that encodes a binding agent according to claim 1 under conditions suitable for the expression of said polypeptide; and ii) purifying said polypeptide from said cell, or its growth environment.

17. A method for increasing catabolic half-life of a binding agent according to claim 1, the method comprising increasing the molecular weight of the binding agent to at least 70 kDa, wherein the molecular weight is determined by 12% SDS-PAGE under reducing or non-reducing conditions.

18. A method according to claim 17, wherein the molecular weight of the binding agent is increased by fusing a peptide to the binding agent.

19. A method according to claim 17, wherein the molecular weight of the binding agent is increased by pegylation.

20. A method according to claim 17, wherein the molecular weight of the binding agent is increased to between 70 to 80 kDa, wherein the molecular weight is determined by 12% SDS-PAGE under reducing or non-reducing conditions.

21. A method according to claim 17, wherein the molecular weight of the binding agent is increased to greater than 80 kDa, wherein the molecular weight is determined by 12% SDS-PAGE under reducing or non-reducing conditions.

22. An isolated nucleic acid molecule comprising the nucleotide sequence set forth in SEQ ID NO: 7 encoding a binding agent wherein said binding agent is a fusion protein and is an agonist of growth hormone receptor.

23. A vector comprising a nucleic acid molecule of claim 22.

24. A vector according to claim 23 wherein the vector is an expression vector.

25. A vector according to claim 24 wherein said vector is an expression vector adapted for prokaryotic gene expression.

26. A vector according to claim 24 wherein said vector is an expression vector adapted for eukaryotic gene expression.

27. A vector according to claim 24 wherein said vector further comprises a nucleotide sequence encoding a secretion signal to facilitate purification of a polypeptide expressed from the vector.

28. An isolated cell comprising a nucleic acid according to claim 22.

29. An isolated cell according to claim 28, wherein the cell is a eukaryotic cell.

30. An isolated cell according to claim 29, wherein said cell is selected from the group consisting of: fungal cell; insect cell; amphibian cell; plant cell and mammalian cell.

31. An isolated cell according to claim 28, wherein said cell is a prokaryotic cell.

32. An isolated cell according to claim 31 wherein said cell is *Escherchia coli*.

33. A polypeptide comprising the amino acid sequence encoded by the isolated nucleic acid molecule of claim 22.

34. A composition comprising the polypeptide according to claim 33, and a pharmaceutically acceptable carrier, excipient or diluent.

35. A method for preparing a polypeptide encoded by SEQ ID NO: 7, the method comprising:
   i) growing a cell according to claim 28 under conditions suitable for the expression of said polypeptide; and
   ii) purifying said polypeptide from said cell, or its growth environment.

* * * * *

SEQUENCE LISTING

```
<160> NUMBER OF SEQ ID NOS: 35

<210> SEQ ID NO 1
<211> LENGTH: 588
<212> TYPE: DNA
<213> ORGANISM: Homo sapiens

<400> SEQUENCE: 1
ttcccaacca ttcccttatc caggcttttt gacaacgcta tgctccgcgc ccatcgtctg      60
caccagctgg cctttgacac ctaccaggag tttgaagaag cctatatccc aaaggaacag     120
aagtattcat tcctgcagaa cccccagacc tccctctgtt tctcagagtc tattccgaca     180
ccctccaaca gggaggaaac acaacagaaa tccaacctag agctgctccg catctccctg     240
```

```
ctgctcatcc agtcgtggct ggagcccgtg cagttcctca ggagtgtctt cgccaacagc      300
ctggtgtacg gcgcctctga cagcaacgtc tatgacctcc taaaggacct agaggaaggc      360
atccaaacgc tgatggggag gctggaagat ggcagccccc ggactgggca gatcttcaag      420
cagacctaca gcaagttcga cacaaactca cacaacgatg acgcactact caagaactac      480
gggctgctct actgcttcag gaaggacatg gacaaggtcg agacattcct gcgcatcgtg      540
cagtgccgct ctgtggaggg cagctgtggc ttcggcggcc gctgataa                  588

<210> SEQ ID NO 2
<211> LENGTH: 390
<212> TYPE: DNA
<213> ORGANISM: Homo sapiens

<400> SEQUENCE: 2
gggaaagaat tcgaaatagt gcaaccagat ccacccattg ccctcaactg gactttactg       60
aacgtcagtt taactgggat tcatgcagat atccaagtga gatgggaagc accacgcaat      120
gcagatattc agaaggatg gatggttctg gagtatgaac ttcaatacaa agaagtaaat       180
gaaactaaat ggaaaatgat ggaccctata ttgacaacat cagttccagt gtactcattg      240
aaagtggata aggaatatga agtgcgtgtg agatccaaac aacgaaactc tggaaattat      300
ggcgagttca gtgaggtgct ctatgtaaca cttcctcaga tgagccaatt tacatgtgaa      360
gaagatttct actgataaaa gcttgggaaa                                      390

<210> SEQ ID NO 3
<211> LENGTH: 972
<212> TYPE: DNA
<213> ORGANISM: ARTIFICIAL SEQUENCE
<220> FEATURE:
<223> OTHER INFORMATION: Description of Artificial Sequence: Synthetic
      GHstopGHR SD100 construct

<400> SEQUENCE: 3
ttcccaacca ttcccttatc caggcttttt gacaacgcta tgctccgcgc ccatcgtctg       60
caccagctgg cctttgacac ctaccaggag tttgaagaag cctatatccc aaaggaacag      120
aagtattcat tcctgcagaa cccccagacc tccctctgtt tctcagagtc tattccgaca      180
ccctccaaca gggaggaaac acaacagaaa tccaacctag agctgctccg catctccctg      240
ctgctcatcc agtcgtggct ggagcccgtg cagttcctca ggagtgtctt cgccaacagc      300
ctggtgtacg gcgcctctga cagcaacgtc tatgacctcc taaaggacct agaggaaggc      360
atccaaacgc tgatggggag gctggaagat ggcagccccc ggactgggca gatcttcaag      420
cagacctaca gcaagttcga cacaaactca cacaacgatg acgcactact caagaactac      480
gggctgctct actgcttcag gaaggacatg gacaaggtcg agacattcct gcgcatcgtg      540
cagtgccgct ctgtggaggg cagctgtggc ttcggcggcc gctgataaaa gggcgaattc      600
gaaatagtgc aaccagatcc acccattgcc ctcaactgga ctttactgaa cgtcagttta      660
actgggattc atgcagatat ccaagtgaga tgggaagcac cacgcaatgc agatattcag      720
aaggatggat ggttctggag tatgaacttc aatacaaag aagtaaatga actaaatgg       780 aaaatgatgg accctatatt gacaacatca gttccagtgt actcattgaa agtggataag      840
gaatatgaag tgcgtgtgag atccaaacaa cgaaactctg gaaattatgg cgagttcagt      900
gaggtgctct atgtaacact tcctcagatg agccaattta catgtgaaga agatttctac      960
tgataaaagc tt                                                          972
```

<210> SEQ ID NO 4
<211> LENGTH: 1020
<212> TYPE: DNA
<213> ORGANISM: ARTIFICIAL SEQUENCE
<220> FEATURE:
<223> OTHER INFORMATION: Description of Artificial Sequence: Synthetic
      GHlinkGHR construct

<400> SEQUENCE: 4

```
ttcccaacca ttcccttatc caggcttttt gacaacgcta tgctccgcgc ccatcgtctg      60
caccagctgg cctttgacac ctaccaggag tttgaagaag cctatatccc aaaggaacag     120
aagtattcat tcctgcagaa cccccagacc tccctctgtt tctcagagtc tattccgaca     180
ccctccaaca gggaggaaac acaacagaaa tccaacctag agctgctccg catctccctg     240
ctgctcatcc agtcgtggct ggagcccgtg cagttcctca ggagtgtctt cgccaacagc     300
ctggtgtacg gcgcctctga cagcaacgtc tatgacctcc taaggaccct agaggaaggc     360
atccaaacgc tgatggggag gctggaagat ggcagccccc ggactgggca gatcttcaag     420
cagacctaca gcaagttcga cacaaactca cacaacgatg acgcactact caagaactac     480
gggctgctct actgcttcag gaaggacatg gacaaggtcg agacattcct gcgcatcgtg     540
cagtgccgct ctgtggaggg cagctgtggc ttcggcggcc gcggtggcgg aggtagtggt     600
ggcggaggta gcggtggcgg aggttctggt ggcggaggtt ccgaattcga aatagtgcaa     660
ccagatccac ccattgccct caactggact ttactgaacg tcagtttaac tgggattcat     720
gcagatatcc aagtgagatg ggaagcacca cgcaatgcag atattcagaa aggatggatg     780
gttctggagt atgaacttca atacaaagaa gtaaatgaaa ctaaatggaa atgatggac     840
cctatattga acatcagt tccagtgtac tcattgaaag tggataagga atatgaagtg     900
cgtgtgagat ccaaacaacg aaactctgga aattatggcg agttcagtga ggtgctctat     960
gtaacacttc ctcagatgag ccaatttaca tgtgaagaag atttctactg ataaaagctt    1020
```

<210> SEQ ID NO 5
<211> LENGTH: 336
<212> TYPE: PRT
<213> ORGANISM: ARTIFICIAL SEQUENCE
<220> FEATURE:
<223> OTHER INFORMATION: Description of Artificial Sequence: Synthetic
      fusion protein

<400> SEQUENCE: 5

```
Phe Pro Thr Ile Pro Leu Ser Arg Leu Phe Asp Asn Ala Met Leu Arg
  1               5                  10                  15

Ala His Arg Leu His Gln Leu Ala Phe Asp Thr Tyr Gln Glu Phe Glu
             20                  25                  30

Glu Ala Tyr Ile Pro Lys Glu Gln Lys Tyr Ser Phe Leu Gln Asn Pro
         35                  40                  45

Gln Thr Ser Leu Cys Phe Ser Glu Ser Ile Pro Thr Pro Ser Asn Arg
     50                  55                  60

Glu Glu Thr Gln Gln Lys Ser Asn Leu Glu Leu Leu Arg Ile Ser Leu
 65                  70                  75                  80

Leu Leu Ile Gln Ser Glu Leu Glu Pro Val Gln Phe Leu Arg Ser Val
                 85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125
```

| Glu | Asp | Gly | Ser | Pro | Arg | Thr | Gly | Gln | Ile | Phe | Lys | Gln | Thr | Tyr | Ser |
| | 130 | | | | 135 | | | | | 140 | | | | | |

| Lys | Phe | Asp | Thr | Asn | Ser | His | Asn | Asp | Asp | Ala | Leu | Leu | Lys | Asn | Tyr |
| 145 | | | | | 150 | | | | | 155 | | | | | 160 |

| Gly | Leu | Leu | Tyr | Cys | Phe | Arg | Lys | Asp | Met | Asp | Lys | Val | Glu | Thr | Phe |
| | | | | 165 | | | | | 170 | | | | | 175 | |

| Leu | Arg | Ile | Val | Gln | Cys | Arg | Ser | Val | Glu | Gly | Ser | Cys | Gly | Phe | Gly |
| | | | 180 | | | | | 185 | | | | | 190 | | |

| Gly | Arg | Gly | Gly | Gly | Ser | Gly | Gly | Gly | Ser | Gly | Gly | Gly |
| | | | 195 | | | | | 200 | | | | | 205 | | |

| Ser | Gly | Gly | Gly | Ser | Glu | Phe | Glu | Ile | Val | Gln | Pro | Asp | Pro |
| 210 | | | | | 215 | | | | | 220 | | | |

| Ile | Ala | Leu | Asn | Glu | Thr | Leu | Leu | Asn | Val | Ser | Leu | Thr | Gly | Ile | His |
| 225 | | | | | 230 | | | | | 235 | | | | | 240 |

| Ala | Asp | Ile | Gln | Val | Arg | Glu | Glu | Ala | Pro | Arg | Asn | Ala | Asp | Ile | Gln |
| | | | | 245 | | | | | 250 | | | | | 255 | |

| Lys | Gly | Glu | Met | Val | Leu | Glu | Tyr | Glu | Leu | Gln | Tyr | Lys | Glu | Val | Asn |
| | | | 260 | | | | | 265 | | | | | 270 | | |

| Glu | Thr | Lys | Glu | Lys | Met | Met | Asp | Pro | Ile | Leu | Thr | Thr | Ser | Val | Pro |
| | | 275 | | | | | 280 | | | | | 285 | | | |

| Val | Tyr | Ser | Leu | Lys | Val | Asp | Lys | Glu | Tyr | Glu | Val | Arg | Val | Arg | Ser |
| | 290 | | | | | 295 | | | | | 300 | | | | |

| Lys | Gln | Arg | Asn | Ser | Gly | Asn | Tyr | Gly | Glu | Phe | Ser | Glu | Val | Leu | Tyr |
| 305 | | | | | 310 | | | | | 315 | | | | | 320 |

| Val | Thr | Leu | Pro | Gln | Met | Ser | Gln | Phe | Thr | Cys | Glu | Glu | Asp | Phe | Tyr |
| | | | | 325 | | | | | 330 | | | | | 335 | |

<210> SEQ ID NO 6
<211> LENGTH: 762
<212> TYPE: DNA
<213> ORGANISM: Homo sapiens

<400> SEQUENCE: 6

```
gggaaagaat tctttctgg aagtgaggcc acagcagcta tccttagcag agcaccctgg      60
agtctgcaaa gtgttaatcc aggcctaaag acaaattctt ctaaggagcc taaattcacc    120
aagtgccgtt cacctgagcg agagactttt tcatgccact ggacagatga ggttcatcat    180
ggtacaaaga acctaggacc catacagctg ttctatacca gaaggaacac tcaagaatgg    240
actcaagaat ggaaagaatg ccctgattat gtttctgctg gggaaaacag ctgttacttt    300
aattcatcgt ttacctccat ctggatacct tattgtatca agctaactag caatggtggt    360
acagtggatg aaaagtgttt ctctgttgat gaaatagtgc aaccagatcc acccattgcc    420
ctcaactgga ctttactgaa cgtcagttta actgggattc atgcagatat ccaagtgaga    480
tgggaagcac cacgcaatgc agatattcag aaaggatgga tggttctgga gtatgaactt    540
caatacaaag aagtaaatga aactaaatgg aaaatgatgg accctatatt gacaacatca    600
gttccagtgt actcattgaa agtggataag gaatatgaag tgcgtgtgag atccaaacaa    660
cgaaactctg gaaattatgg cgagttcagt gaggtgctct atgtaacact tcctcagatg    720
agccaattta catgtgaaga agatttctac tgataaaagc tt                       762
```

<210> SEQ ID NO 7
<211> LENGTH: 1398
<212> TYPE: DNA
<213> ORGANISM: ARTIFICIAL SEQUENCE

<220> FEATURE:
<223> OTHER INFORMATION: Description of Artificial Sequence: Synthetic
      GHlinkGHRflec construct

<400> SEQUENCE: 7

```
ttcccaacca ttcccttatc caggcttttt gacaacgcta tgctccgcgc ccatcgtctg    60
caccagctgg cctttgacac ctaccaggag tttgaagaag cctatatccc aaaggaacag   120
aagtattcat tcctgcagaa cccccagacc tccctctgtt tctcagagtc tattccgaca   180
ccctccaaca gggaggaaac acaacagaaa tccaacctag agctgctccg catctccctg   240
ctgctcatcc agtcgtggct ggagcccgtg cagttcctca ggagtgtctt cgccaacagc   300
ctggtgtacg cgcctctga cagcaacgtc tatgacctcc taaaggacct agaggaaggc   360
atccaaacgc tgatggggag ctggaagat ggcagccccc ggactgggca gatcttcaag   420
cagacctaca gcaagttcga cacaaactca cacaacgatg acgcactact caagaactac   480
gggctgctct actgcttcag gaaggacatg gacaaggtcg agacattcct gcgcatcgtg   540
cagtgccgct ctgtggaggg cagctgtggc ttcggcggcc gcggtggcgg aggtagtggt   600
ggcggaggta gcggtggcgg aggttctggt ggcggaggtt ccgaattctt ttctggaagt   660
gaggccacag cagctatcct tagcagagca ccctggagtc tgcaaagtgt taatccaggc   720
ctaaagacaa attcttctaa ggagcctaaa ttcaccaagt gccgttcacc tgagcgagag   780
acttttttcat gccactggac agatgaggtt catcatggta caaagaaacct aggacccata   840
cagctgttct ataccagaag gaacactcaa gaatggactc aagaatggaa agaatgccct   900
gattatgttt ctgctgggga aaacagctgt tactttaatt catcgtttac ctccatctgg   960
ataccttatt gtatcaagct aactagcaat ggtggtacag tggatgaaaa gtgtttctct  1020
gttgatgaaa tagtgcaacc agatccaccc attgccctca actggactt actgaacgtc  1080
agtttaactg ggattcatgc agatatccaa gtgagatggg aagcaccacg caatgcagat  1140
attcagaaag gatggatggt tctggagtat gaacttcaat acaaagaagt aaatgaaact  1200
aaatggaaaa tgatggaccc tatattgaca acatcagttc cagtgtactc attgaaagtg  1260
gataaggaat atgaagtgcg tgtgagatcc aaacaacgaa actctggaaa ttatggcgag  1320
ttcagtgagg tgctctatgt aacacttcct cagatgagcc aatttacatg tgaagaagat  1380
ttctactgat aaaagctt                                                1398
```

<210> SEQ ID NO 8
<211> LENGTH: 1157
<212> TYPE: DNA
<213> ORGANISM: ARTIFICIAL SEQUENCE
<220> FEATURE:
<223> OTHER INFORMATION: Description of Artificial Sequence: Synthetic
      construct

<400> SEQUENCE: 8

```
gggaaagagc tcaaggagaa aataaaatgg ggggttctca tcatcatcat catcatggta    60
tggctagcat gactggtgga cagcaaatgg gtcgggatct gtacgacgat gacgataagg   120
atccaacccct tttcccaacc attcccttat ccaggctttt tgacaacgct atgctccgcg   180
cccatcgtct gcaccagctg gcctttgaca cctaccagga gtttgaagaa gcctatatcc   240
caaaggaaca gaagtattca ttcctgcaga accccccagac ctccctctgt ttctcagagt   300
ctattccgac accctccaac agggaggaaa cacaacagaa atccaaccta gagctgctcc   360
gcatctccct gctgctcatc cagtcgtggc tggagcccgt gcagttcctc aggagtgtct   420
```

```
tcgccaacag cctggtgtac ggcgcctctg acagcaacgt ctatgacctc ctaaaggacc    480
tagaggaagg catccaaacg ctgatgggga ggctggaaga tggcagcccc cggactgggc    540
agatcttcaa gcagacctac agcaagttcg acacaaactc acacaacgat gacgcactac    600
tcaagaacta cgggctgctc tactgcttca ggaaggacat ggacaaggtc gagacattcc    660
tgcgcatcgt gcagtgccgc tctgtggagg gcagctgtgg cttcggcggc cgcggtggcg    720
gaggtagtgg tggcggaggt agcggtggcg gaggttctgg tggcggaggt tccgaattcg    780
aaatagtgca accagatcca cccattgccc tcaactggac tttactgaac gtcagtttaa    840
ctgggattca tgcagatatc caagtgagat gggaagcacc acgcaatgca gatattcaga    900
aaggatggat ggttctggag tatgaacttc aatacaaaga agtaaatgaa actaaatgga    960
aaatgatgga ccctatattg acaacatcag ttccagtgta ctcattgaaa gtggataagg    1020
aatatgaagt gcgtgtgaga tccaaacaac gaaactctgg aaattatggc gagttcagtg    1080
aggtgctcta tgtaacactt cctcagatga gccaatttac atgtgaagaa gatttctact    1140
gataaaagct tgggaaa                                                   1157
```

<210> SEQ ID NO 9  
<211> LENGTH: 740  
<212> TYPE: DNA  
<213> ORGANISM: ARTIFICIAL SEQUENCE  
<220> FEATURE:  
<223> OTHER INFORMATION: Description of Artificial Sequence: Synthetic construct

<400> SEQUENCE: 9

```
gagctcaagg agaaaataaa atggggggtt ctcatcatca tcatcatcat ggtatggcta     60
gcatgactgg tggacagcaa atgggtcggg atctgtacga cgatgacgat aaggatccaa    120
cccttttccc aaccattccc ttatccaggc tttttgacaa cgctatgctc cgcgcccatc    180
gtctgcacca gctggccttt gacacctacc aggagtttga agaagcctat atcccaaagg    240
aacagaagta ttcattcctg cagaaccccc agacctccct ctgtttctca gagtctattc    300
cgacaccctc caacagggag gaaacacaac agaaatccaa cctagagctg ctccgcatct    360
ccctgctgct catccagtcg tggctggagc ccgtgcagtt cctcaggagt gtcttcgcca    420
acagcctggt gtacggcgcc tctgacagca acgtctatga cctcctaaag gacctagagg    480
aaggcatcca aacgctgatg gggaggctgg aagatggcag cccccggact gggcagatct    540
tcaagcagac ctacagcaag ttcgacacaa actcacacaa cgatgacgca ctactcaaga    600
actacgggct gctctactgc ttcaggaagg acatggacaa ggtcgagaca ttcctgcgca    660
tcgtgcagtg ccgctctgtg gagggcagct gtggcttcgg cggccgctga taaagggcg     720 aattcaattc gaagcttggc                                                740
```

<210> SEQ ID NO 10  
<211> LENGTH: 190  
<212> TYPE: PRT  
<213> ORGANISM: Homo sapiens

<400> SEQUENCE: 10

Val Pro Pro Gly Glu Asp Ser Lys Asp Val Ala Ala Pro His Arg Gln
1               5                   10                  15

Pro Leu Thr Ser Ser Glu Arg Ile Asp Lys Gln Ile Arg Tyr Ile Leu
                20                  25                  30

Asp Gly Ile Ser Ala Leu Arg Lys Glu Thr Cys Asn Lys Ser Asn Met
            35                  40                  45

```
Cys Glu Ser Ser Lys Glu Ala Leu Ala Glu Asn Asn Leu Asn Leu Pro
     50                  55                  60
Lys Met Ala Glu Lys Asp Gly Cys Phe Gln Ser Gly Phe Asn Glu Glu
 65                  70                  75                  80
Thr Cys Leu Val Lys Ile Ile Thr Gly Leu Glu Phe Glu Val Tyr
                 85                  90                  95
Leu Glu Tyr Leu Gln Asn Arg Phe Glu Ser Ser Glu Glu Gln Ala Arg
             100                 105                 110
Ala Val Gln Met Ser Thr Lys Val Leu Ile Gln Phe Leu Gln Lys Lys
             115                 120                 125
Ala Lys Asn Leu Asp Ala Ile Thr Thr Pro Asp Pro Thr Thr Asn Ala
         130                 135                 140
Ser Leu Leu Thr Lys Leu Gln Ala Gln Asn Gln Trp Leu Gln Asp Met
145                 150                 155                 160
Thr Thr His Leu Ile Leu Arg Ser Phe Lys Glu Phe Leu Gln Ser Ser
                 165                 170                 175
Leu Arg Ala Leu Arg Gln Met Gly Gly Arg Val Asp Lys Gly
             180                 185                 190

<210> SEQ ID NO 11
<211> LENGTH: 1791
<212> TYPE: DNA
<213> ORGANISM: Homo sapiens

<400> SEQUENCE: 11
gaacttctag atccatgtgg ttatatcagt cctgaatctc cagttgtaca acttcattct      60
aatttcactg cagtttgtgt gctaaaggaa aaatgtatgg attattttca tgtaaatgct     120
aattacattg tctggaaaac aaaccatttt actattccta aggagcaata tactatcata     180
aacagaacag catccagtgt cacctttaca gatatagctt cattaaatat tcagctcact     240
tgcaacattc ttacattcgg acagcttgaa cagaatgttt atggaatcac ataatttca     300 ggcttgcctc cagaaaaacc taaaaatttg agttgcattg tgaacgaggg gaagaaaatg     360
aggtgtgagt gggatggtgg aagggaaaca cacttggaga caaacttcac tttaaaatct     420
gaatgggcaa cacacaagtt tgctgattgc aaagcaaaac gtgacacccc cacctcatgc     480
actgttgatt attctactgt gtattttgtc aacattgaag tctgggtaga agcagagaat     540
gcccttggga aggttacatc agatcatatc aattttgatc ctgtatataa agtgaagccc     600
aatccgccac ataatttatc agtgatcaac tcagaggaac tgtctagtat cttaaaattg     660
acatggacca acccaagtat taagagtgtt ataatactaa aatataacat tcaatatagg     720
accaaagatg cctcaacttg gagccagatt cctcctgaag acacagcatc cacccgatct     780
tcattcactg tccaagacct taaaccttt acagaatatg tgtttaggat tcgctgtatg     840
aaggaagatg gtaagggata ctggagtgac tggagtgaag aagcaagtgg gatcacctat     900
gaagatagac catctaaagc accaagtttc tggtataaaa tagatccatc ccatactcaa     960
ggctacagaa ctgtacaact cgtgtggaag acattgcctc cttttgaagc caatggaaaa    1020
atcttggatt atgaagtgac tctcacaaga tggaaatcac atttacaaaa ttacacagtt    1080
aatgccacaa actgacagt aaatctcaca atgatcgct atctagcaac cctaacagta    1140
agaaatcttg ttggcaaatc agatgcagct gttttaacta cccctgcctg tgactttcaa    1200
gctactcacc ctgtaatgga tcttaaagca ttccccaaag ataacatgct ttgggtggaa    1260
tggactactc caagggaatc tgtaaagaaa tatatacttg agtggtgtgt gttatcagat    1320
```

-continued

```
aaagcaccct gtatcacaga ctggcaacaa gaagatggta ccgtgcatcg cacctattta    1380
agagggaact tagcagagag caaatgctat ttgataacag ttactccagt atatgctgat    1440
ggaccaggaa gccctgaatc cataaaggca taccttaaac aagctccacc ttccaaagga    1500
cctactgttc ggacaaaaaa agtagggaaa acgaagctg tcttagagtg ggaccaactt     1560
cctgttgatg ttcagaatgg atttatcaga aattatacta tattttatag aaccatcatt    1620
ggaaatgaaa ctgctgtgaa tgtggattct tcccacacag aatatacatt gtcctctttg    1680
actagtgaca cattgtacat ggtacgaatg gcagcataca cagatgaagg tgggaaggat    1740
ggtccagaat tcactttac taccccaaag tttgctcaag gagaaattga a              1791
```

<210> SEQ ID NO 12
<211> LENGTH: 807
<212> TYPE: PRT
<213> ORGANISM: ARTIFICIAL SEQUENCE
<220> FEATURE:
<223> OTHER INFORMATION: Description of Artificial Sequence: IL-6/gp130
    fusion polypeptide

<400> SEQUENCE: 12

```
Val Pro Pro Gly Glu Asp Ser Lys Asp Val Ala Ala Pro His Arg Gln
1               5                   10                  15

Pro Leu Thr Ser Ser Glu Arg Ile Asp Lys Gln Ile Arg Tyr Ile Leu
            20                  25                  30

Asp Gly Ile Ser Ala Leu Arg Lys Glu Thr Cys Asn Lys Ser Asn Met
        35                  40                  45

Cys Glu Ser Ser Lys Glu Ala Leu Ala Glu Asn Asn Leu Asn Leu Pro
    50                  55                  60

Lys Met Ala Glu Lys Asp Gly Cys Phe Gln Ser Gly Phe Asn Glu Glu
65                  70                  75                  80

Thr Cys Leu Val Lys Ile Ile Thr Gly Leu Leu Glu Phe Glu Val Tyr
                85                  90                  95

Leu Glu Tyr Leu Gln Asn Arg Phe Glu Ser Ser Glu Glu Gln Ala Arg
            100                 105                 110

Ala Val Gln Met Ser Thr Lys Val Leu Ile Gln Phe Leu Gln Lys Lys
        115                 120                 125

Ala Lys Asn Leu Asp Ala Ile Thr Thr Pro Asp Pro Thr Thr Asn Ala
    130                 135                 140

Ser Leu Leu Thr Lys Leu Gln Ala Gln Asn Gln Trp Leu Gln Asp Met
145                 150                 155                 160

Thr Thr His Leu Ile Leu Arg Ser Phe Lys Glu Phe Leu Gln Ser Ser
                165                 170                 175

Leu Arg Ala Leu Arg Gln Met Gly Gly Arg Gly Gly Gly Ser Gly
            180                 185                 190

Gly Gly Gly Ser Gly Gly Gly Ser Gly Gly Gly Ser Val Asp
        195                 200                 205

Glu Leu Leu Asp Pro Cys Gly Tyr Ile Ser Pro Glu Ser Pro Val Val
    210                 215                 220

Gln Leu His Ser Asn Phe Thr Ala Val Cys Val Leu Lys Glu Lys Cys
225                 230                 235                 240

Met Asp Tyr Phe His Val Asn Ala Asn Tyr Ile Val Trp Lys Thr Asn
                245                 250                 255

His Phe Thr Ile Pro Lys Glu Gln Tyr Thr Ile Ile Asn Arg Thr Ala
            260                 265                 270
```

```
Ser Ser Val Thr Phe Thr Asp Ile Ala Ser Leu Asn Ile Gln Leu Thr
        275                 280                 285

Cys Asn Ile Leu Thr Phe Gly Gln Leu Glu Gln Asn Val Tyr Gly Ile
        290                 295                 300

Thr Ile Ile Ser Gly Leu Pro Pro Glu Lys Pro Lys Asn Leu Ser Cys
305                 310                 315                 320

Ile Val Asn Glu Gly Lys Lys Met Arg Cys Glu Trp Asp Gly Gly Arg
                325                 330                 335

Glu Thr His Leu Glu Thr Asn Phe Thr Leu Lys Ser Glu Trp Ala Thr
        340                 345                 350

His Lys Phe Ala Asp Cys Lys Ala Lys Arg Asp Thr Pro Thr Ser Cys
        355                 360                 365

Thr Val Asp Tyr Ser Thr Val Tyr Phe Val Asn Ile Glu Val Trp Val
        370                 375                 380

Glu Ala Glu Asn Ala Leu Gly Lys Val Thr Ser Asp His Ile Asn Phe
385                 390                 395                 400

Asp Pro Val Tyr Lys Val Lys Pro Asn Pro Pro His Asn Leu Ser Val
                405                 410                 415

Ile Asn Ser Glu Glu Leu Ser Ser Ile Leu Lys Leu Thr Trp Thr Asn
                420                 425                 430

Pro Ser Ile Lys Ser Val Ile Ile Leu Lys Tyr Asn Ile Gln Tyr Arg
        435                 440                 445

Thr Lys Asp Ala Ser Thr Trp Ser Gln Ile Pro Pro Glu Asp Thr Ala
        450                 455                 460

Ser Thr Arg Ser Ser Phe Thr Val Gln Asp Leu Lys Pro Phe Thr Glu
465                 470                 475                 480

Tyr Val Phe Arg Ile Arg Cys Met Lys Glu Asp Gly Lys Gly Tyr Trp
                485                 490                 495

Ser Asp Trp Ser Glu Glu Ala Ser Gly Ile Thr Tyr Glu Asp Arg Pro
        500                 505                 510

Ser Lys Ala Pro Ser Phe Trp Tyr Lys Ile Asp Pro Ser His Thr Gln
        515                 520                 525

Gly Tyr Arg Thr Val Gln Leu Val Trp Lys Thr Leu Pro Pro Phe Glu
        530                 535                 540

Ala Asn Gly Lys Ile Leu Asp Tyr Glu Val Thr Leu Thr Arg Trp Lys
545                 550                 555                 560

Ser His Leu Gln Asn Tyr Thr Val Asn Ala Thr Lys Leu Thr Val Asn
                565                 570                 575

Leu Thr Asn Asp Arg Tyr Leu Ala Thr Leu Thr Val Arg Asn Leu Val
                580                 585                 590

Gly Lys Ser Asp Ala Ala Val Leu Thr Ile Pro Ala Cys Asp Phe Gln
        595                 600                 605

Ala Thr His Pro Val Met Asp Leu Lys Ala Phe Pro Lys Asp Asn Met
        610                 615                 620

Leu Trp Val Glu Trp Thr Thr Pro Arg Glu Ser Val Lys Lys Tyr Ile
625                 630                 635                 640

Leu Glu Trp Cys Val Leu Ser Asp Lys Ala Pro Cys Ile Thr Asp Trp
                645                 650                 655

Gln Gln Glu Asp Gly Thr Val His Arg Thr Tyr Leu Arg Gly Asn Leu
        660                 665                 670

Ala Glu Ser Lys Cys Tyr Leu Ile Thr Val Thr Pro Val Tyr Ala Asp
        675                 680                 685

Gly Pro Gly Ser Pro Glu Ser Ile Lys Ala Tyr Leu Lys Gln Ala Pro
```

-continued

```
              690                 695                 700
Pro Ser Lys Gly Pro Thr Val Arg Thr Lys Val Gly Lys Asn Glu
705                 710                 715                 720

Ala Val Leu Glu Trp Asp Gln Leu Pro Val Asp Val Gln Asn Gly Phe
                725                 730                 735

Ile Arg Asn Tyr Thr Ile Phe Tyr Arg Thr Ile Ile Gly Asn Glu Thr
                740                 745                 750

Ala Val Asn Val Asp Ser Ser His Thr Glu Tyr Thr Leu Ser Ser Leu
                755                 760                 765

Thr Ser Asp Thr Leu Tyr Met Val Arg Met Ala Ala Tyr Thr Asp Glu
        770                 775                 780

Gly Gly Lys Asp Gly Pro Glu Phe Thr Phe Thr Thr Pro Lys Phe Ala
785                 790                 795                 800

Gln Gly Glu Ile Glu Lys Leu
                805
```

<210> SEQ ID NO 13
<211> LENGTH: 1497
<212> TYPE: DNA
<213> ORGANISM: ARTIFICIAL SEQUENCE
<220> FEATURE:
<223> OTHER INFORMATION: Description of Artificial Sequence: gp 130
      domain 1 deletion

<400> SEQUENCE: 13

| | | | | |
|---|---|---|---|---|
| atttcaggct | tgcctccaga | aaaacctaaa | aatttgagtt | gcattgtgaa cgaggggaag | 60 |
| aaaatgaggt | gtgagtggga | tggtggaagg | gaaacacact | tggagacaaa cttcacttta | 120 |
| aaatctgaat | gggcaacaca | caagtttgct | gattgcaaag | caaaacgtga cacccccacc | 180 |
| tcatgcactg | ttgattattc | tactgtgtat | tttgtcaaca | ttgaagtctg ggtagaagca | 240 |
| gagaatgccc | ttgggaaggt | tacatcagat | catatcaatt | ttgatcctgt atataaagtg | 300 |
| aagcccaatc | cgccacataa | tttatcagtg | atcaactcag | aggaactgtc tagtatctta | 360 |
| aaattgacat | ggaccaaccc | aagtattaag | agtgttataa | tactaaaata taacattcaa | 420 |
| tataggacca | aagatgcctc | aacttggagc | cagattcctc | ctgaagacac agcatccacc | 480 |
| cgatcttcat | tcactgtcca | agaccttaaa | ccttttacag | aatatgtgtt taggattcgc | 540 |
| tgtatgaagg | aagatggtaa | gggatactgg | agtgactgga | gtgaagaagc aagtgggatc | 600 |
| acctatgaag | atagaccatc | taaagcacca | agtttctggt | ataaaataga tccatcccat | 660 |
| actcaaggct | acagaactgt | acaactcgtg | tggaagacat | gcctcccttt tgaagccaat | 720 |
| ggaaaaatct | tggattatga | agtgactctc | acaagatgga | atcacatttt acaaaattac | 780 |
| acagttaatg | ccacaaaact | gacagtaaat | ctcacaaatg | atcgctatct agcaacccta | 840 |
| acagtaagaa | atcttgttgg | caaatcagat | gcagctgttt | taactatccc tgcctgtgac | 900 |
| tttcaagcta | ctcaccctgt | aatggatctt | aaagcattcc | ccaaagataa catgctttgg | 960 |
| gtggaatgga | ctactccaag | ggaatctgta | aagaaatata | tacttgagtg gtgtgtgtta | 1020 |
| tcagataaag | caccctgtat | cacagactgg | caacaagaag | atggtaccgt gcatcgcacc | 1080 |
| tatttaagag | ggaacttagc | agagagcaaa | tgctatttga | taacagttac tccagtatat | 1140 |
| gctgatggac | aggaagccc | tgaatccata | aaggcatacc | ttaaacaagc tccaccttcc | 1200 |
| aaaggaccta | ctgttcggac | aaaaaaagta | gggaaaaacg | aagctgtctt agagtgggac | 1260 |
| caacttcctg | ttgatgttca | aatggattt | atcagaaatt | atactatatt ttatagaacc | 1320 |
| atcattggaa | atgaaactgc | tgtgaatgtg | gattcttccc | acacagaata tacattgtcc | 1380 |

-continued

| | |
|---|---|
| tctttgacta gtgacacatt gtacatggta cgaatggcag catacacaga tgaaggtggg | 1440 |
| aaggatggtc cagaattcac ttttactacc ccaaagtttg ctcaaggaga aattgaa | 1497 |

<210> SEQ ID NO 14
<211> LENGTH: 1191
<212> TYPE: DNA
<213> ORGANISM: Homo sapiens

<400> SEQUENCE: 14

| | |
|---|---|
| aatccgccac ataatttatc agtgatcaac tcagaggaac tgtctagtat cttaaaattg | 60 |
| acatggacca acccaagtat taagagtgtt ataatactaa aatataacat tcaatatagg | 120 |
| accaaagatg cctcaacttg gagccagatt cctcctgaag acacagcatc cacccgatct | 180 |
| tcattcactg tccaagacct taaacctttt acagaatatg tgtttaggat tcgctgtatg | 240 |
| aaggaagatg gtaagggata ctggagtgac tggagtgaag aagcaagtgg gatcaccctat | 300 |
| gaagatagac catctaaagc accaagtttc tggtataaaa tagatccatc ccatactcaa | 360 |
| ggctacagaa ctgtacaact cgtgtggaag acattgcctc cttttgaagc caatggaaaa | 420 |
| atcttggatt atgaagtgac tctcacaaga tggaaatcac atttacaaaa ttacacagtt | 480 |
| aatgccacaa aactgacagt aaatctcaca aatgatcgct atctagcaac cctaacagta | 540 |
| agaaatcttg ttggcaaatc agatgcagct gttttaacta tccctgcctg tgactttcaa | 600 |
| gctactcacc ctgtaatgga tcttaaagca ttccccaaag ataacatgct ttgggtggaa | 660 |
| tggactactc caagggaatc tgtaaagaaa tatatacttg agtggtgtgt gttatcagat | 720 |
| aaagcaccct gtatcacaga ctggcaacaa gaagatggta ccgtgcatcg cacctattta | 780 |
| agagggaact tagcagagag caaatgctat ttgataacga ttactccagt atatgctgat | 840 |
| ggaccaggaa gccctgaatc cataaaggca taccttaaac aagctccacc ttccaaagga | 900 |
| cctactgttc ggacaaaaaa agtagggaaa acgaagctg tcttagagtg ggaccaactt | 960 |
| cctgttgatg ttcagaatgg atttatcaga aattatacta tattttatag aaccatcatt | 1020 |
| ggaaatgaaa ctgctgtgaa tgtggattct tcccacacag aatatacatt gtcctctttg | 1080 |
| actagtgaca cattgtacat ggtacgaatg gcagcataca cagatgaagg tgggaaggat | 1140 |
| ggtccagaat tcactttttac taccccaaag tttgctcaag gagaaattga a | 1191 |

<210> SEQ ID NO 15
<211> LENGTH: 945
<212> TYPE: DNA
<213> ORGANISM: ARTIFICIAL SEQUENCE
<220> FEATURE:
<223> OTHER INFORMATION: Description of Artificial Sequence: Chi 1A2 chimera

<400> SEQUENCE: 15

| | |
|---|---|
| ttcccaacca ttcccttatc caggcttttt gacaacgcta tgctccgcgc ccatcgtctg | 60 |
| caccagctgg cctttgacac ctaccaggag tttgaagaag cctatatccc aaaggaacag | 120 |
| aagtattcat tcctgcagaa cccccagacc tccctctgtt tctcagagtc tattccgaca | 180 |
| ccctccaaca gggaggaaac acaacagaaa tccaacctag agctgctccg catctccctg | 240 |
| ctgctcatcc agtcgtggct ggagcccgtg cagttcctca ggagtgtctt cgccaacagc | 300 |
| ctggtgtacg gcgcctctga cagcaacgtc tatgacctcc taaggaccct agaggaaggc | 360 |
| atccaaacgc tgatggggag gctggaagat ggcagccccc ggactgggca gatcttcaag | 420 |
| cagacctaca gcaagttcga cacaaaactca cacaacgatg acgcactact caagaactac | 480 |

-continued

```
gggctgctct actgcttcag gaaggacatg gacaaggtcg agacattcct gcgcatcgtg    540
cagtgccgct ctgtggaggg cagctgtggc ttcgaaatag tgcaaccaga tccacccatt    600
gccctcaact ggactttact gaacgtcagt ttaactggga ttcatgcaga tatccaagtg    660
agatgggaag caccacgcaa tgcagatatt cagaaggat ggatggttct ggagtatgaa     720
cttcaataca aagaagtaaa tgaaactaaa tggaaaatga tggaccctat attgacaaca    780
tcagttccag tgtactcatt gaaagtggat aaggaatatg aagtgcgtgt gagatccaaa    840
caacgaaact ctggaaatta tggcgagttc agtgaggtgc tctatgtaac acttcctcag    900
atgagccaat ttacatgtga agaagatttc tactgataaa agctt                    945
```

<210> SEQ ID NO 16
<211> LENGTH: 311
<212> TYPE: PRT
<213> ORGANISM: ARTIFICIAL SEQUENCE
<220> FEATURE:
<223> OTHER INFORMATION: Description of Artificial Sequence: Chi 1A2
      chimera

<400> SEQUENCE: 16

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Glu
            180                 185                 190

Ile Val Gln Pro Asp Pro Pro Ile Ala Leu Asn Trp Thr Leu Leu Asn
        195                 200                 205

Val Ser Leu Thr Gly Ile His Ala Asp Ile Gln Val Arg Trp Glu Ala
    210                 215                 220

Pro Arg Asn Ala Asp Ile Gln Lys Gly Trp Met Val Leu Glu Tyr Glu
225                 230                 235                 240

Leu Gln Tyr Lys Glu Val Asn Glu Thr Lys Trp Lys Met Met Asp Pro
                245                 250                 255

Ile Leu Thr Thr Ser Val Pro Val Tyr Ser Leu Lys Val Asp Lys Glu
            260                 265                 270
```

```
Tyr Glu Val Arg Val Arg Ser Lys Gln Arg Asn Ser Gly Asn Tyr Gly
        275                 280                 285

Glu Phe Ser Glu Val Leu Tyr Val Thr Leu Pro Gln Met Ser Gln Phe
        290                 295                 300

Thr Cys Glu Glu Asp Phe Tyr
305                 310

<210> SEQ ID NO 17
<211> LENGTH: 5
<212> TYPE: PRT
<213> ORGANISM: ARTIFICIAL SEQUENCE
<220> FEATURE:
<223> OTHER INFORMATION: Description of Artificial Sequence: Synthetic
      peptide

<400> SEQUENCE: 17

Gly Gly Gly Gly Ser
1               5

<210> SEQ ID NO 18
<211> LENGTH: 23
<212> TYPE: DNA
<213> ORGANISM: ARTIFICIAL SEQUENCE
<220> FEATURE:
<223> OTHER INFORMATION: Description of Artificial Sequence: Synthetic
      primer

<400> SEQUENCE: 18
ttcccaacca ttcccttatc cag                                           23

<210> SEQ ID NO 19
<211> LENGTH: 36
<212> TYPE: DNA
<213> ORGANISM: ARTIFICIAL SEQUENCE
<220> FEATURE:
<223> OTHER INFORMATION: Description of Artificial Sequence: Synthetic
      primer

<400> SEQUENCE: 19
ttatcagcgg ccgccgaagc cacagctgcc ctccac                             36

<210> SEQ ID NO 20
<211> LENGTH: 67
<212> TYPE: DNA
<213> ORGANISM: ARTIFICIAL SEQUENCE
<220> FEATURE:
<223> OTHER INFORMATION: Description of Artificial Sequence: Synthetic
      oligonucleotide

<400> SEQUENCE: 20
ggccgcggtg gcggaggtag tggtggcgga ggtagcggtg gcggaggttc tggtggcgga   60
ggttccg                                                             67

<210> SEQ ID NO 21
<211> LENGTH: 67
<212> TYPE: DNA
<213> ORGANISM: ARTIFICIAL SEQUENCE
<220> FEATURE:
<223> OTHER INFORMATION: Description of Artificial Sequence: Synthetic
      oligonucleotide

<400> SEQUENCE: 21
aattcggaac ctccgccacc agaacctccg ccaccgctac ctccgccacc actacctccg   60
ccaccgc                                                             67
```

<210> SEQ ID NO 22
<211> LENGTH: 47
<212> TYPE: DNA
<213> ORGANISM: ARTIFICIAL SEQUENCE
<220> FEATURE:
<223> OTHER INFORMATION: Description of Artificial Sequence: Synthetic primer

<400> SEQUENCE: 22
gggaaagagc tcaaggagaa aataaaatgg ggggttctca tcatcat            47

<210> SEQ ID NO 23
<211> LENGTH: 22
<212> TYPE: DNA
<213> ORGANISM: ARTIFICIAL SEQUENCE
<220> FEATURE:
<223> OTHER INFORMATION: Description of Artificial Sequence: Synthetic primer

<400> SEQUENCE: 23
gccaagcttc gaattgaatt cg                                        22

<210> SEQ ID NO 24
<211> LENGTH: 31
<212> TYPE: DNA
<213> ORGANISM: ARTIFICIAL SEQUENCE
<220> FEATURE:
<223> OTHER INFORMATION: Description of Artificial Sequence: Synthetic primer

<400> SEQUENCE: 24 gtaccccag gagaagattc caaagatgta g                               31

<210> SEQ ID NO 25
<211> LENGTH: 41
<212> TYPE: DNA
<213> ORGANISM: ARTIFICIAL SEQUENCE
<220> FEATURE:
<223> OTHER INFORMATION: Description of Artificial Sequence: Synthetic primer

<400> SEQUENCE: 25
tgagggctct tcggcaaatg ggcggccgct gataagtcga c                   41

<210> SEQ ID NO 26
<211> LENGTH: 41
<212> TYPE: DNA
<213> ORGANISM: ARTIFICIAL SEQUENCE
<220> FEATURE:
<223> OTHER INFORMATION: Description of Artificial Sequence: Synthetic primer

<400> SEQUENCE: 26
cagctgaata gtcgccggcg ggtaaacggc ttctcgggag t                   41

<210> SEQ ID NO 27
<211> LENGTH: 41
<212> TYPE: DNA
<213> ORGANISM: ARTIFICIAL SEQUENCE
<220> FEATURE:
<223> OTHER INFORMATION: Description of Artificial Sequence: Synthetic primer

<400> SEQUENCE: 27
gtcgacttat cagcggccgc ccatttgccg aagagccctc a                   41

<210> SEQ ID NO 28
<211> LENGTH: 34
<212> TYPE: DNA
<213> ORGANISM: ARTIFICIAL SEQUENCE
<220> FEATURE:
<223> OTHER INFORMATION: Description of Artificial Sequence: Synthetic
      primer

<400> SEQUENCE: 28
gggaaagtcg acgaacttct agatccatgt ggtt                              34

<210> SEQ ID NO 29
<211> LENGTH: 45
<212> TYPE: DNA
<213> ORGANISM: ARTIFICIAL SEQUENCE
<220> FEATURE:
<223> OTHER INFORMATION: Description of Artificial Sequence: Synthetic
      primer

<400> SEQUENCE: 29
ccaaagtttg ctcaaggaga aattgaatga taaaagcttg ggaaa                  45

<210> SEQ ID NO 30
<211> LENGTH: 45
<212> TYPE: DNA
<213> ORGANISM: ARTIFICIAL SEQUENCE
<220> FEATURE:
<223> OTHER INFORMATION: Description of Artificial Sequence: Synthetic
      primer

<400> SEQUENCE: 30
aaagggttcg aaaatagtaa gttaaagagg aactcgtttg aaacc                  45

<210> SEQ ID NO 31
<211> LENGTH: 45
<212> TYPE: DNA
<213> ORGANISM: ARTIFICIAL SEQUENCE
<220> FEATURE:
<223> OTHER INFORMATION: Description of Artificial Sequence: Synthetic
      primer

<400> SEQUENCE: 31
tttcccaagc ttttatcatt caatttctcc ttgagcaaac tttgg                  45

<210> SEQ ID NO 32
<211> LENGTH: 67
<212> TYPE: DNA
<213> ORGANISM: ARTIFICIAL SEQUENCE
<220> FEATURE:
<223> OTHER INFORMATION: Description of Artificial Sequence: Synthetic
      primer

<400> SEQUENCE: 32
ggccgcggtg gcggaggtag tggtggcgga ggtagcggtg gcggaggttc tggtggcgga  60
ggttccg                                                           67

<210> SEQ ID NO 33
<211> LENGTH: 67
<212> TYPE: DNA
<213> ORGANISM: ARTIFICIAL SEQUENCE
<220> FEATURE:
<223> OTHER INFORMATION: Description of Artificial Sequence: Synthetic
      primer

<400> SEQUENCE: 33
tcgacggaac ctccgccacc agaacctccg ccaccgctac ctccgccacc actacctccg  60

```
-continued
ccaccgc                                                                67

<210> SEQ ID NO 34
<211> LENGTH: 30
<212> TYPE: DNA
<213> ORGANISM: ARTIFICIAL SEQUENCE
<220> FEATURE:
<223> OTHER INFORMATION: Description of Artificial Sequence: Synthetic
      primer

<400> SEQUENCE: 34
gggaaagtcg acatttcagg cttgcctcca                                       30

<210> SEQ ID NO 35
<211> LENGTH: 31
<212> TYPE: DNA
<213> ORGANISM: ARTIFICIAL SEQUENCE
<220> FEATURE:
<223> OTHER INFORMATION: Description of Artificial Sequence: Synthetic
      primer

<400> SEQUENCE: 35
gggaaagtcg acaatccgcc acataattta t                                     31
```